(12) United States Patent
Kim et al.

(10) Patent No.: US 10,978,376 B2
(45) Date of Patent: Apr. 13, 2021

(54) SENSING DEVICE AND METHOD FOR FABRICATING THE SAME

(71) Applicant: ELECTRONICS AND TELECOMMUNICATIONS RESEARCH INSTITUTE, Daejeon (KR)

(72) Inventors: Yong Hee Kim, Daejeon (KR); Sang-Don Jung, Daejeon (KR)

(73) Assignee: ELECTRONICS AND TELECOMMUNICATIONS RESEARCH INSTITUTE, Daejeon (KR)

(*) Notice: Subject to any disclaimer, the term of this patent is extended or adjusted under 35 U.S.C. 154(b) by 10 days.

(21) Appl. No.: 16/700,955

(22) Filed: Dec. 2, 2019

(65) Prior Publication Data
US 2020/0235039 A1    Jul. 23, 2020

(30) Foreign Application Priority Data

Jan. 18, 2019 (KR) .................. 10-2019-0007170
Apr. 26, 2019 (KR) .................. 10-2019-0049394

(51) Int. Cl.
*H01L 23/48* (2006.01)
*H01L 23/29* (2006.01)
*H01L 21/02* (2006.01)
*H01L 23/00* (2006.01)
*H01L 23/31* (2006.01)

(52) U.S. Cl.
CPC ...... *H01L 23/481* (2013.01); *H01L 21/02315* (2013.01); *H01L 23/29* (2013.01); *H01L 23/3171* (2013.01); *H01L 24/80* (2013.01); *H01L 2924/181* (2013.01)

(58) Field of Classification Search
CPC ... H01L 23/481; H01L 23/29; H01L 23/3171; H01L 21/02315; H01L 24/80; H01L 2924/181
USPC .......................................................... 257/777
See application file for complete search history.

(56) References Cited

U.S. PATENT DOCUMENTS 7,048,890 B2 * 5/2006 Coehoorn .............. B82Y 25/00
                                                      210/222
7,884,623 B2    2/2011 Kim et al.
8,969,099 B2    3/2015 Ah et al.
(Continued)

FOREIGN PATENT DOCUMENTS

KR    20110134720 A    12/2011
KR     101663685 B1    10/2016
KR    20170101606 A     9/2017

OTHER PUBLICATIONS

Alan K. Mo et al., "Understanding the Mechanism of Solvent-Mediated Adhesion of Vacuum Deposited Au and Pt Thin Films onto PMMA Substrate", Advanced Functional Materials, vol. 23, 2013.

(Continued)

*Primary Examiner* — Tu-Tu V Ho

(57) ABSTRACT

Provided is a sensing device and a method for fabricating the same. The sensing device includes a first sensor including a first substrate, first electrodes, and a first passivation layer and a second sensor disposed on the first sensor and including a second substrate, second electrodes, and a second passivation layer. The second sensor is connected to the first sensor through a chemical bonding.

20 Claims, 27 Drawing Sheets

(56) References Cited

U.S. PATENT DOCUMENTS

| | | |
|---|---|---|
| 9,173,281 B2 | 10/2015 | Kim et al. |
| 10,312,215 B2 | 6/2019 | Kim et al. |
| 2013/0033671 A1 | 2/2013 | Schadt et al. |
| 2017/0164853 A1 | 6/2017 | Kim et al. |

OTHER PUBLICATIONS

Ikjoo Byun et al., "Transfer of thin Au films to polydimethylsiloxane (PDMS) with reliable bonding using (3-mercaptopropyl) trimethoxysilane (MPTMS) as a molecular adhesive", Journal of Micromechanics and Microengineering, vol. 23, 2013.

John D. Yeager et al., "Microstructural characterization of thin gold films on a polyimide substrate", Thin Solid Films, vol. 518, 2010.

Stefan B. Rieger et al., "Concept and Development of an Electronic Framework Intended for Electrode and Surrounding Environment Characterization In Vivo", Sensors, vol. 17, 2017.

Tae-Il Kim et al., "Injectable, Cellular-Scale Optoelectronics with Applications for Wireless Optogenetics", Science, vol. 30, Apr. 12, 2013.

Takayuki Komori et al., "Fabrication of Au Micro-Electrodes on Polyimide Films Using Transfer Printing Techniques", Applied Mechanics and Materials, vol. 300-301, pp. 1368-1371, 2013.

Yong Hee Kim et al., "Fluoropolymer-based Flexible Neural Prosthetic Electrodes for Reliable Neural Interfacing", ACS Applied Materials & Interfaces, 2017.

\* cited by examiner

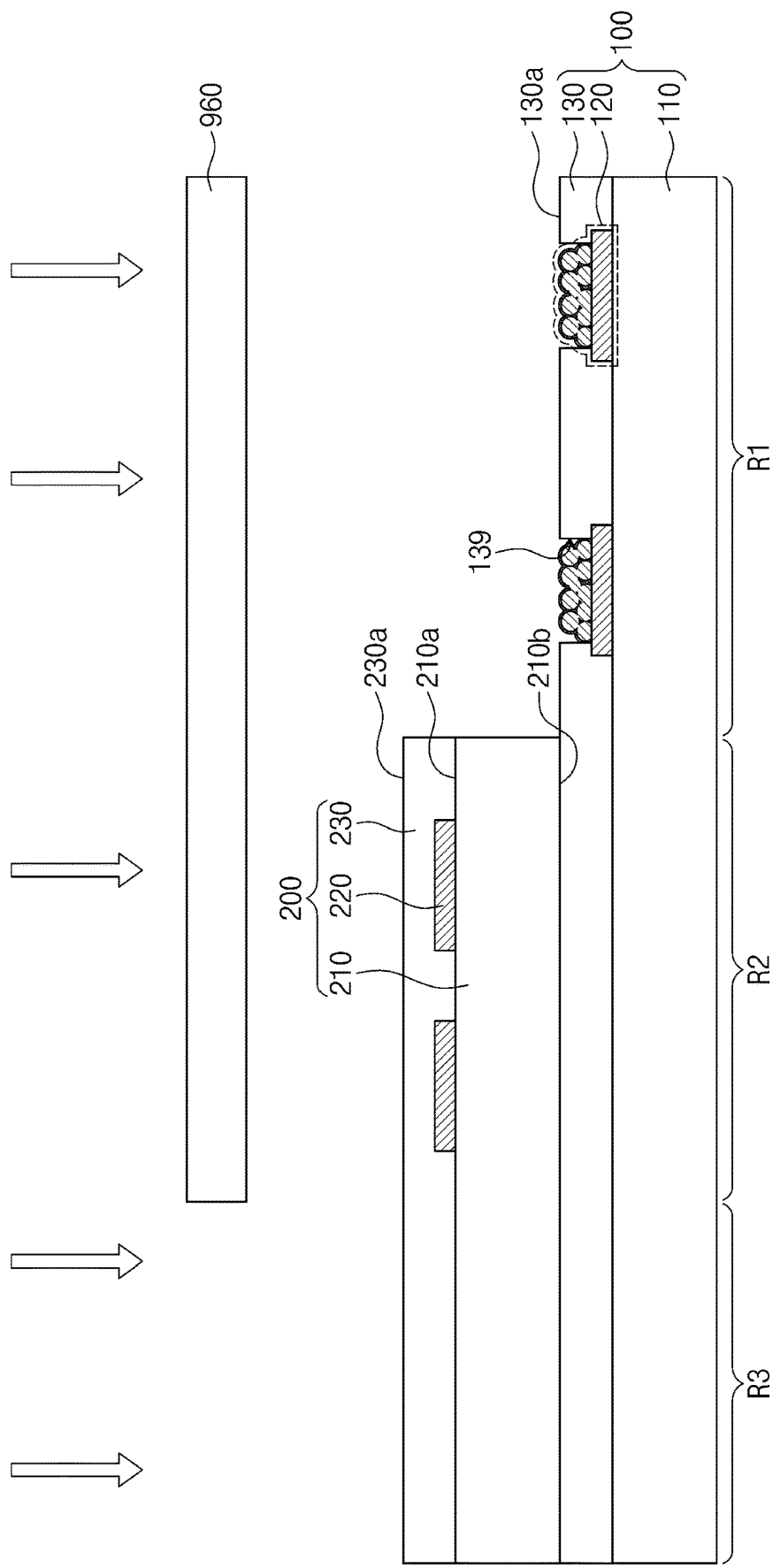

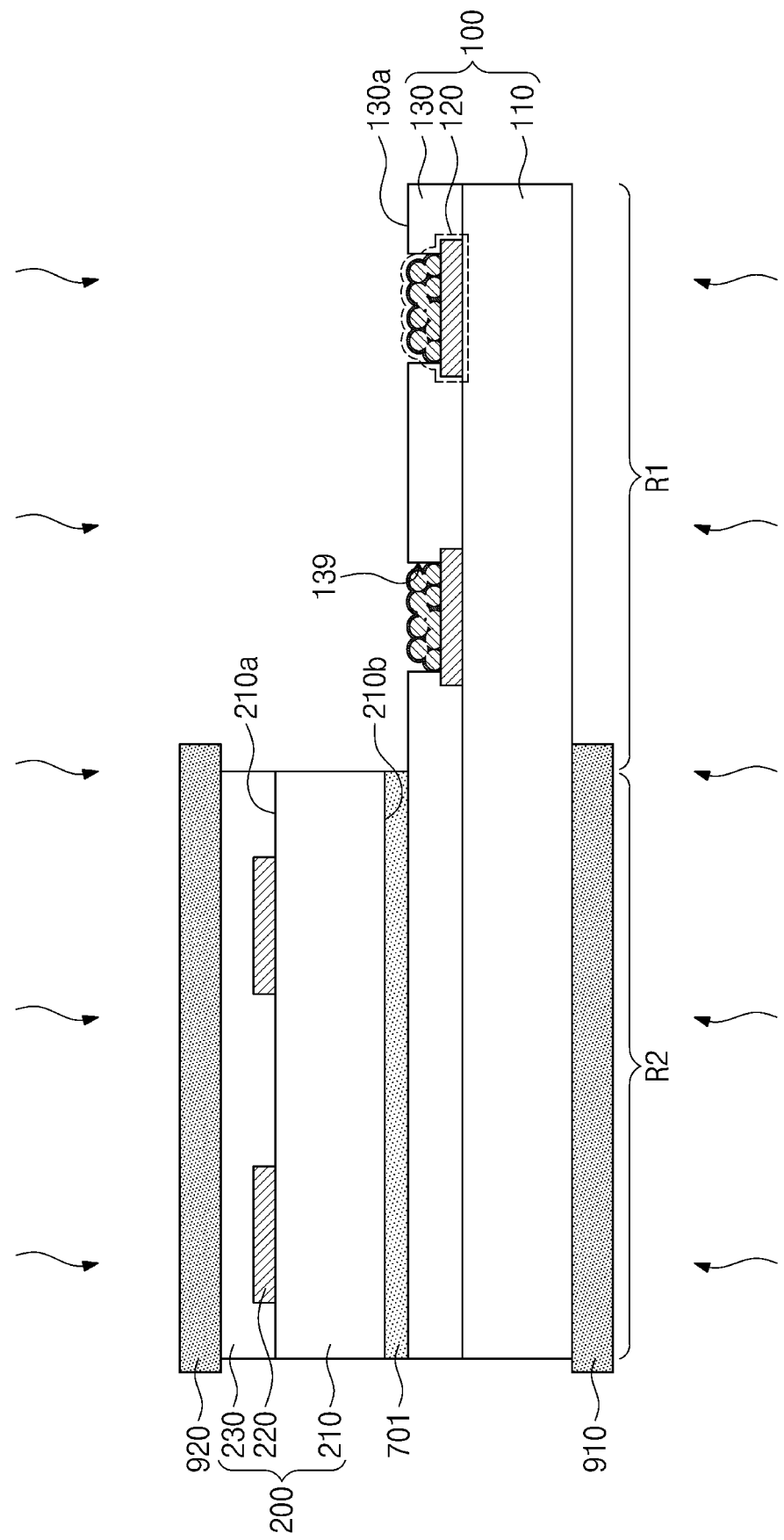

SENSING DEVICE AND METHOD FOR FABRICATING THE SAME

CROSS-REFERENCE TO RELATED APPLICATIONS

This U.S. non-provisional patent application claims priority under 35 U.S.C. § 119 of Korean Patent Application No. 10-2019-0007170, filed on Jan. 18, 2019 and 10-2019-0049394, filed on Apr. 26, 2019, the entire contents of which are hereby incorporated by reference.

BACKGROUND

The present disclosure herein relates to a method for fabricating a sensing device including an electrode, and more particularly, to a method for fabricating a sensing device using a plasma treatment process.

An electrode may provide an electrical stimulation to an object to be detected or detect a signal. The electrode is implanted in vital nervous tissues, and the like and used for recording a neural signal or for applying an electrical stimulation. As the demand for electrodes have diversified, there has been an increasing demand for multi-channelization and stability of the electrodes.

An sensing device may be used in vivo or in vitro. Here, when the sensing device has a too large size, it is difficult to be used in living organisms. Thus, a demand for miniaturization of the sensing device is increasing.

SUMMARY

The present disclosure provides a method for fabricating a sensing device that is improved in durability and miniaturized.

The present disclosure also provides a method for fabricating a sensing device that is simplified.

The object of the present disclosure is not limited to the aforesaid, but other objects not described herein will be clearly understood by those skilled in the art from descriptions below.

The present disclosure relates to a sensing device and a method for fabricating the same. An embodiment of the inventive concept provides a sensing device including: a first sensor including a first substrate, first electrodes, and a first passivation layer; and a second sensor disposed on the first sensor and including a second substrate, second electrodes, and a second passivation layer, wherein the second sensor is connected to the first sensor through a chemical bonding.

In an embodiment, the first electrodes and the first passivation layer may be disposed on a top surface of the first substrate, the second substrate may be disposed on a top surface of the first passivation layer, and the chemical bonding may be provided between the first passivation layer and the second substrate.

In an embodiment, the first substrate may have a first area and a second area in view of a plane, wherein the second sensor may overlap the second area of the first substrate in view of the plane, and the second electrodes may be disposed on the first area of the first substrate.

In an embodiment, the first sensor may include a neural electrode sensor, and the second sensor may include a chemical sensor or a physical sensor.

In an embodiment, the sensing device may further include a third sensor disposed on the second sensor and connected to the second sensor through a chemical bonding, wherein the third sensor may include a third substrate, third electrodes, and a third passivation layer.

In an embodiment, the chemical bonding may include crosslinked bonding or covalent bonding.

In an embodiment, the second substrate may have a bottom surface that physically contacts a top surface of the first substrate, and the chemical bonding may be provided between the first substrate and the second substrate.

In an embodiment, the first electrodes and the first passivation layer may be disposed on a bottom surface of the first substrate.

In an embodiment, the first substrate may have first areas and a second area, the first electrodes may be disposed on the first areas of the first substrate, the first passivation layer may cover the second area of the first substrate, and the first passivation layer may be chemically bonded to a top surface of the second area of the first substrate.

In an embodiment, the first substrate may include a fluorine-based polymer, and the first passivation layer may include a photosensitive polymer.

In an embodiment of the inventive concept, a method for fabricating a sensing device includes: preparing a first sensor; performing a first plasma treatment process on a first surface of the first sensor; performing a second plasma treatment process on a second surface of a second sensor; and forming a chemical bonding between the first surface of the first sensor and the second surface of the second sensor, wherein the first sensor includes a first substrate, first electrodes, and a first passivation layer, and the second sensor includes a second substrate, second electrodes, and a second passivation layer.

In an embodiment, first radicals may be formed on the first surface of the first sensor by the first plasma treatment process, second radicals may be formed on the second surface of the second sensor by the second plasma treatment process, and the chemical bonding may be formed by reaction of the first radicals and the second radicals.

In an embodiment, the forming of the chemical bonding may be performed by a thermocompression process.

In an embodiment, the method may further include disposing the second sensor on the first sensor so that the second substrate faces the first passivation layer, wherein the chemical bonding may be formed between the second substrate and the first passivation layer.

In an embodiment, the preparing of the first sensor may include: preparing a first substrate having a first area and a second area; forming a first electrode layer on the first substrate, wherein the first electrode layer directly physically contacts a top surface of the first area of the first substrate; performing a plasma treatment process on the first substrate and the first electrode layer; forming a first passivation layer covering the first substrate and the first electrode layer; and performing an exposure process and a development process on the first passivation layer to form a first opening in the first passivation layer, wherein the performing of the exposure process may include forming a chemical bonding between a top surface of the second area of the first substrate and the first passivation layer.

In an embodiment of the inventive concept, a sensing device includes: a first sensor including a first substrate, first electrodes, and a first passivation layer; a second sensor disposed on the first sensor and including a second substrate, second electrodes, and a second passivation layer, and a film disposed between the first sensor and the second sensor, wherein the first sensor is connected to the film through a first chemical bonding, and the second sensor is connected to the film through a second chemical bonding.

In an embodiment, the first substrate may have first areas and a second area, the first electrodes may be respectively disposed on the first areas of the first substrate, the first passivation layer may cover the second area of the first substrate, and the first passivation layer may be chemically bonded to a top surface of the second area of the first substrate.

In an embodiment, the first chemical bonding may include crosslinked bonding or covalent bonding, and the second chemical bonding may include crosslinked bonding or covalent bonding.

In an embodiment, the first electrodes and the first passivation layer may be disposed on a top surface of the first substrate, the second substrate may be disposed on a top surface of the first passivation layer, and the film may be disposed between the first passivation layer and the second substrate.

In an embodiment, the first electrodes and the first passivation layer may be disposed on a bottom surface of the first substrate, the film may be disposed between a top surface of the first substrate and a bottom surface of the second substrate, and the first chemical bonding may be provided between the first substrate and the film.

BRIEF DESCRIPTION OF THE FIGURES

The accompanying drawings are included to provide a further understanding of the inventive concept, and are incorporated in and constitute a part of this specification. The drawings illustrate exemplary embodiments of the inventive concept and, together with the description, serve to explain principles of the inventive concept. In the drawings:

FIGS. 8A to 8C are views for explaining a method for fabricating a sensing device according to an embodiment;

FIGS. 10A and 10B are views for explaining a method for fabricating a sensing device according to further another embodiment;

DETAILED DESCRIPTION

Figure 1A:
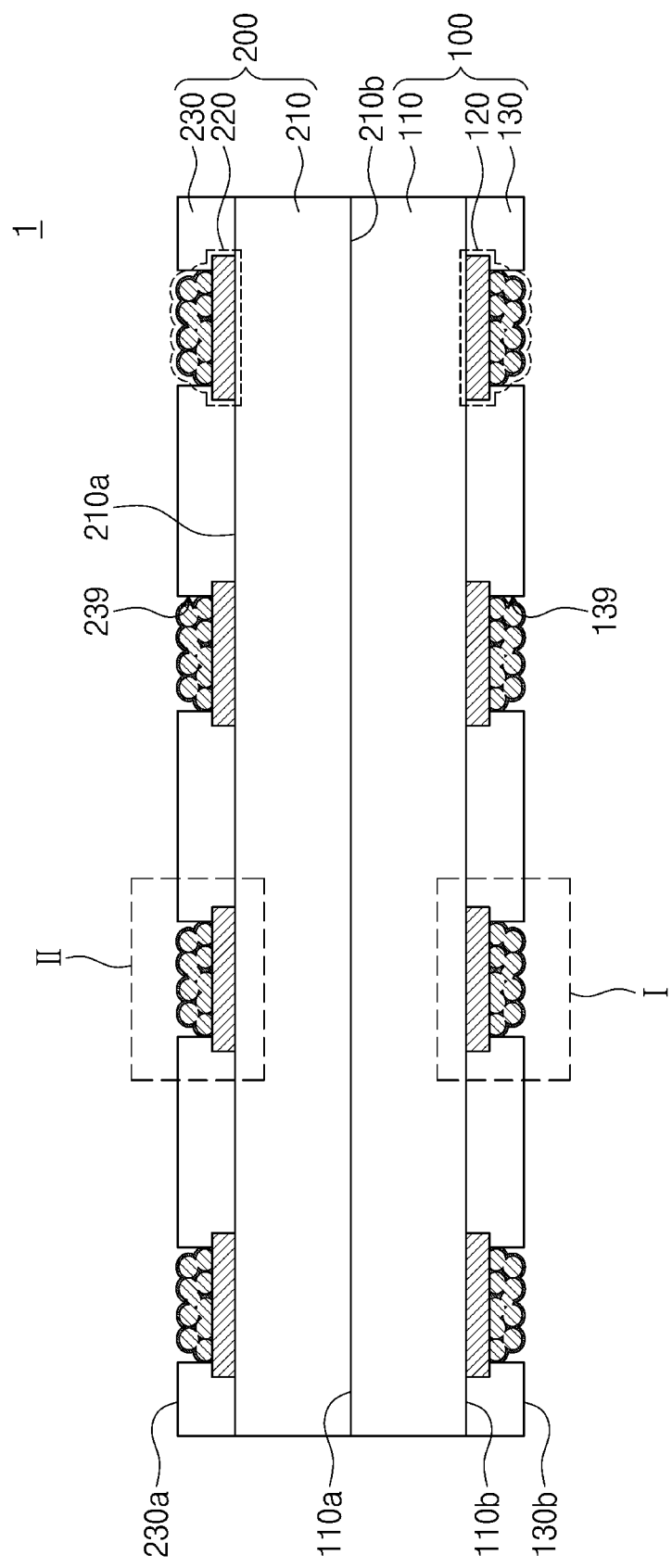
FIG. 1A is a view for explaining a sensing device according to an embodiment of the inventive concept.

Exemplary embodiments of the inventive concept will be described with reference to the accompanying drawings so as to sufficiently understand constitutions and effects of the inventive concept. The present invention may, however, be embodied in different forms and should not be construed as limited to the embodiments set forth herein. Rather, these embodiments are provided so that this disclosure will be thorough and complete, and will fully convey the scope of the present invention to those skilled in the art. Further, the present invention is only defined by scopes of claims. A person with ordinary skill in the technical field of the present invention pertains will be understood that the present invention can be carried out under any appropriate environments.

In the following description, the technical terms are used only for explaining a specific exemplary embodiment while not limiting the present invention. In this specification, the terms of a singular form may comprise plural forms unless specifically mentioned. The meaning of 'comprises' and/or 'comprising' specifies a component, a step, an operation and/or an element does not exclude other components, steps, operations and/or elements.

In the specification, it will be understood that when a layer (or film) is referred to as being 'on' another layer or substrate, it can be directly on the other layer or substrate, or intervening layers may also be present.

Also, though terms like a first, a second, and a third are used to describe various regions and layers (or films) in various embodiments of the inventive concept, the regions and the layers are not limited to these terms. These terms are used only to discriminate one region or layer (or film) from another region or layer (or film). Therefore, a layer referred to as a first layer in one embodiment can be referred to as a second layer in another embodiment. An embodiment described and exemplified herein includes a complementary embodiment thereof. Like reference numerals refer to like elements throughout.

Unless terms used in embodiments of the present invention are differently defined, the terms may be construed as meanings that are commonly known to a person skilled in the art.

Hereinafter, a sensing device according to the inventive concept will be described with reference to the accompanying drawings.

Figure 1B:
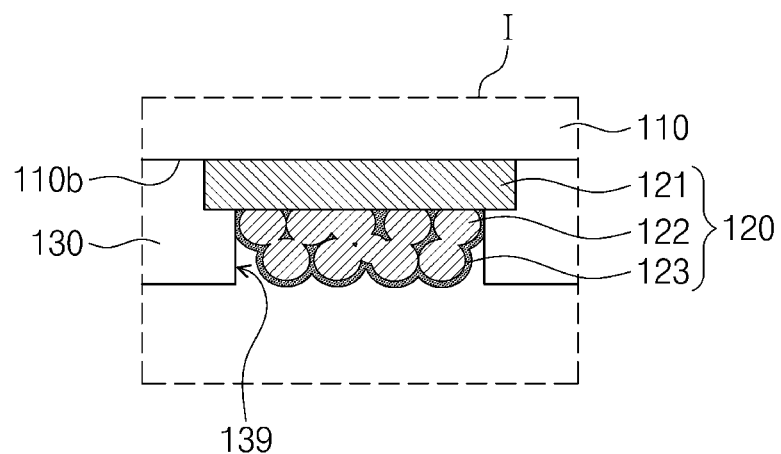
FIG. 1B is a view for explaining a first electrode according to an embodiment, i.e., an enlarged view of an area I of FIG. 1A.

FIG. 1A is a view for explaining a sensing device according to an embodiment of the inventive concept. FIG. 1B is a view for explaining a first electrode according to an embodiment, i.e., an enlarged view of an area I of FIG. 1A.

Figure 1C:
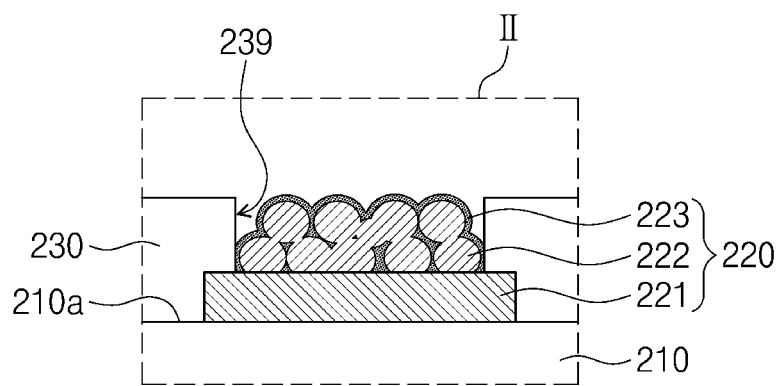
FIG. 1C is a view for explaining a second electrode according to an embodiment, i.e., an enlarged view of an area II of FIG. 1A.

FIG. 1C is a view for explaining a second electrode according to an embodiment, i.e., an enlarged view of an area II of FIG. 1A.

Referring to FIGS. 1A, 1B, and 1C, a sensing device 1 may include a first sensor 100 and a second sensor 200, which are bonded to each other. The first sensor 100 may be a neural electrode sensor, and the neural electrode sensor may include neural electrode arrays. In this specification, the neural electrode sensor may represent a sensor including a neural electrode that will be described below. The first sensor 100 may be used in in-vivo or in-vitro neural interface fields. The first sensor 100 may include a first substrate 110, a first electrode 120, and a first passivation layer 130. The first substrate 110 may include a fluorine-based polymer and have an insulation property. In this specification, the fluorine-based polymer may be a fluorohydrocarbon polymer and may have a plurality of carbon-fluorine (C—F) bonds. For example, the fluorine-based polymer may include fluorinated ethylene-propylene (FEP), perfluoroalkoxy polymer (PFA), and/or polytetrafluoroethylene (PTFE).

The first electrode 120 may be disposed on a bottom surface 110b of the first substrate 110. The first electrode 120 may be provided in plurality to form an electrode array. Each of the electrodes 120 may be a neural electrode. In this specification, the neural electrode may be used to provide an electrical stimulation to a biomaterial or to measure or record an electrical signal (e.g., a neural signal) of the biomaterial. The biomaterial may include neural cells and/or neural tissues. For example, one of the first electrodes 120 may provide an electrical stimulation to the first biomaterial or measure/record an electrical signal, and the other of the first electrodes 120 may provide an electrical stimulation to the second biomaterial or measure/record an electrical signal. The second biomaterial may be different from the first biomaterial. Thus, the sensing device 1 may sense neural signals of various biomaterials.

At least one of the first electrodes 120 may include a first electrode layer 121, a first internal electrode 122, and a first external electrode 123 as illustrated in FIG. 1B. The first electrode layer 121 may be disposed on the bottom surface 110b of the first substrate 110. The first electrode layer 121 may include a conductive thin film. The first electrode 120 may include a metal such as, for example, gold (Au) and be provided as a single layer. The first internal electrode 122 may be disposed on the bottom surface of the first electrode layer 121. The first internal electrode may have a porous structure. For example, the first internal electrode 122 may have pores therein. Thus, the first internal electrode 122 may have a density less than that of the first electrode layer 121. The first internal electrode 122 may include the same metal material as the first electrode layer 121. The first internal electrode 122 may include, for example, gold (Au) or a gold-platinum (AuPt) alloy. The first external electrode 123 may be disposed on the first internal electrode 122 to cover a surface of the first internal electrode 122. The first external electrode 123 may be formed by applying a metal material on the first internal electrode 122. The first external electrode 123 may include a material different from that of each of the first electrode layer and the first internal electrode 122. The first external electrode 123 may include, for example, iridium (Ir). Since the first external electrode 123 is provided, electrical characteristics of the first sensor 100 may be more improved. For another example, the first external electrode 123 may not be provided.

The first passivation layer 130 may be disposed on the bottom surface 110b of the first substrate 110. The first passivation layer 130 may further cover a sidewall of the first electrode layer 121 and a bottom surface of an edge area of the first electrode layer 121. The first passivation layer 130 may have a first opening 139. The first opening 139 may pass through the first passivation layer 130 to expose the bottom surface of the first electrode layer 121. The first internal electrode 122 and the first external electrode 123 may be disposed within the first opening 139 of the first passivation layer 130. The first passivation layer 130 may include an insulative polymer. The first passivation layer 130 may include, for example, a fluorine-based polymer. According to an embodiment, the first passivation layer 130 may be chemically bonded to the first substrate 110. For example, covalent bonding or crosslinked bonding may be provided between the first substrate 110 and the first passivation layer 130. In this case, bonding force between the first substrate 110 and the first passivation layer 130 may be improved.

Referring again to FIG. 1A, the second sensor 200 may be disposed on a first surface of the first sensor 100. The first surface of the first sensor 100 may correspond to a top surface 110a of the first substrate 110. The second sensor 200 may be the same kind of sensor as the first sensor 100. For example, the second sensor 200 may be a neural electrode sensor. The second sensor 200 may perform the same function and role as the first sensor 100. The second sensor 200 may be used in the in-vivo or in-vitro neural interface fields.

The second sensor 200 may include a second substrate 210, a second electrode 220, and a second passivation layer 230. The second substrate 210 may include a fluorine-based polymer and have an insulation property. The fluorine-based polymer may include a material as previously described in the examples of the first substrate 110. The second substrate 210 may be disposed on the top surface 110a of the first substrate 110. The second substrate 210 may have a top surface 210a and a bottom surface 210b, which face each other. The bottom surface 210b of the second substrate 210 may physically contact the top surface 110a of the first substrate 110. The second substrate 210 may be connected to the first substrate through a chemical bonding. For example, covalent bonding or crosslinked bonding may be provided between the first substrate 110 and the second substrate 210. bonding force between the first substrate 110 and the second substrate 210 may be improved by the chemical bonding. Thus, the second sensor 200 may be firmly bonded to the first sensor 100, and the sensing device 1 may have durability and stability. The sensing device 1 may be inserted into a human body or attached to a living body and thus be used without side effects.

The second substrate 220 may be disposed on the top surface 210a of the second substrate 210. The second electrode 220 may be provided in plurality to form an electrode array. The second electrode 220 may be neural electrodes. For example, one of the second electrodes 220 may provide an electrical stimulation to a third biomaterial or measure/record an electrical signal, and the other of the first electrodes 120 may provide an electrical stimulation to a fourth biomaterial or measure/record an electrical signal. The fourth biomaterial may be the same as or different from the third biomaterial. The fourth biomaterial may be the same as or different from the first biomaterial. The fourth biomaterial may be the same as or different from the second biomaterial.

The more the number of electrodes 120 and 220 provided in the sensing device 1 increases, the more accuracy and sensitivity of the sensing device 1 may be improved. However, when each of the electrodes 120 and 220 decreases in size, each of the electrodes 120 and 220 may be reduced in accuracy and sensitivity. When the first electrodes 120 are disposed on the same surface as the second electrodes 220 (for example, the top surface 210a of the second substrate 210), the sensing device 1 may increase in size (for example, a planar area). According to embodiments, since the first electrodes 120 are disposed on the bottom surface 110b of the first substrate 110, the sensing device 1 may be used as a double-sided neural electrode sensor. For example, the second electrodes 220 may be exposed on a top surface of the sensing device 1, and the first electrodes 120 may be exposed on a bottom surface of the sensing device 1. Here, the top surface of the sensing device 1 may correspond to the top surface 230a of the second passivation layer 230, and the bottom surface of the sensing device 1 may correspond to the bottom surface 130b of the first passivation layer 130. Since the sensing device 1 includes the first electrodes 120 and the second electrodes 220, the total number of electrodes 120 and 220 may increase without increasing in size of each of the electrodes 120 and 220. The electrodes 120 and 220 may be improved in degree of integration. Thus, the sensing device 1 may be improved in accuracy and sensitivity, and the sensing device 1 may be miniaturized.

At least one of the second electrodes 220 may include a second electrode layer 221, a second internal electrode 222, and a second external electrode 223 as illustrated in FIG. 1C. The second electrode layer 221 may include a conductive thin film. The second electrode layer 221 may include a metal such as, for example, gold (Au). The second internal electrode 222 may be disposed on the top surface of the second electrode layer 221. The second internal electrode may have a porous structure. For example, the second internal electrode 222 may have pores therein. Thus, the second internal electrode 222 may have a density less than that of the second electrode layer 221. The second internal electrode 222 may include the same metal material as the second electrode layer 221. The second internal electrode 222 may include gold (Au) or a gold-platinum (AuPt) alloy. The second external electrode 223 may be disposed on the second internal electrode 222 to cover a surface of the second internal electrode 222. A metal may be applied on the second internal electrode 222 to form the second external electrode 223. The second external electrode 223 may include a material different from that of each of the second electrode layer and the second internal electrode 222. The second external electrode 223 may include, for example, iridium (Ir). Since the second external electrode 223 is provided, electrical characteristics of the second sensor 200 may be more improved. For another example, the second external electrode 223 may not be provided.

The second passivation layer 230 may be disposed on the top surface 210a of the second substrate 210. The second passivation layer 230 may further cover a sidewall of the second electrode layer 221 and a top surface of an edge area of the second electrode layer 221. The second passivation layer 230 may have a second opening 239. The second opening 239 may pass through the second passivation layer 230 to expose the top surface of the second electrode layer 221. The first internal electrode 122 and the first external electrode 123 may be disposed within the second opening 239 of the first passivation layer 130. The second passivation layer 230 may protect the second substrate 210 and the second electrode layer 221. The second passivation layer 230 may have an insulation property. The second passivation layer 230 may include, for example, a fluorine-based polymer. According to an embodiment, the second passivation layer 230 may be chemically bonded to the second substrate 210. For example, covalent bonding or crosslinked bonding may be provided between the second substrate 210 and the second passivation layer 230. In this case, bonding force between the second substrate 210 and the second passivation layer 230 may be improved.

According to embodiments, the first substrate 110, the second substrate 210, the first passivation layer 130, and the second passivation layer 230 may have high durability against chemicals. The chemicals may include a strong acid or a strong base. The sensing device 1 may be used in various environments. For example, the sensing device 1 may be used in the presence of the chemicals.

Figure 2A:
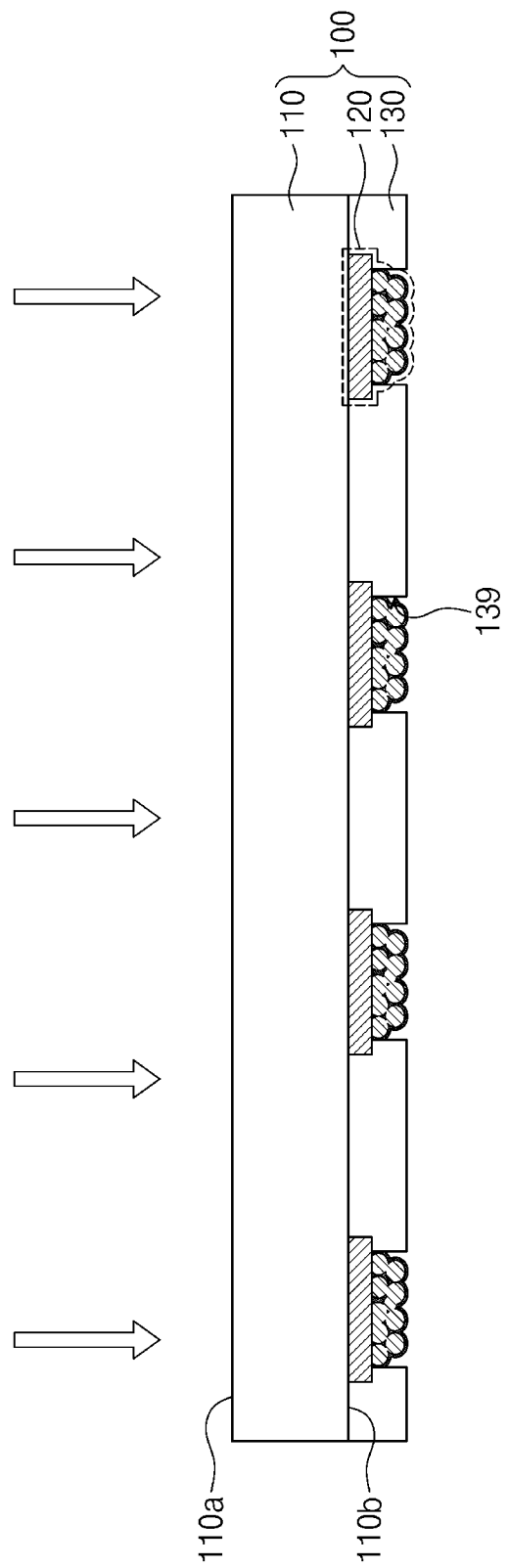
FIGS. 2A to 2C are views for explaining a method for fabricating a sensing device according to an embodiment.
Figure 2B:
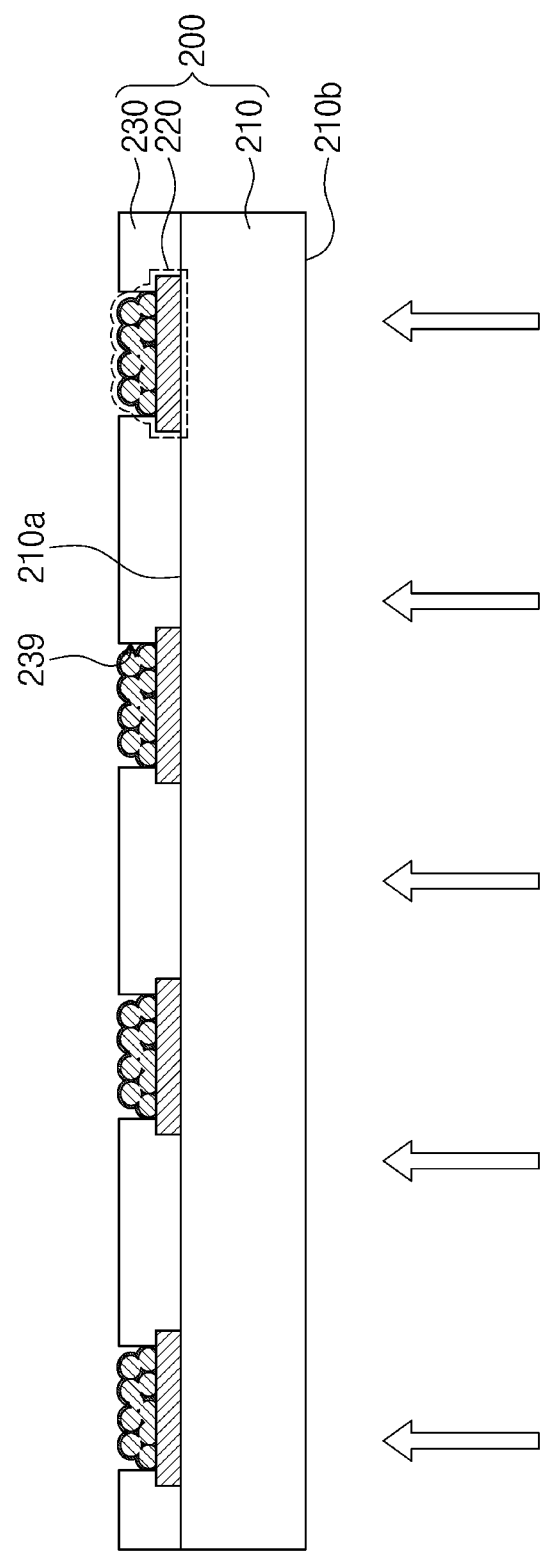
Figure 2C:
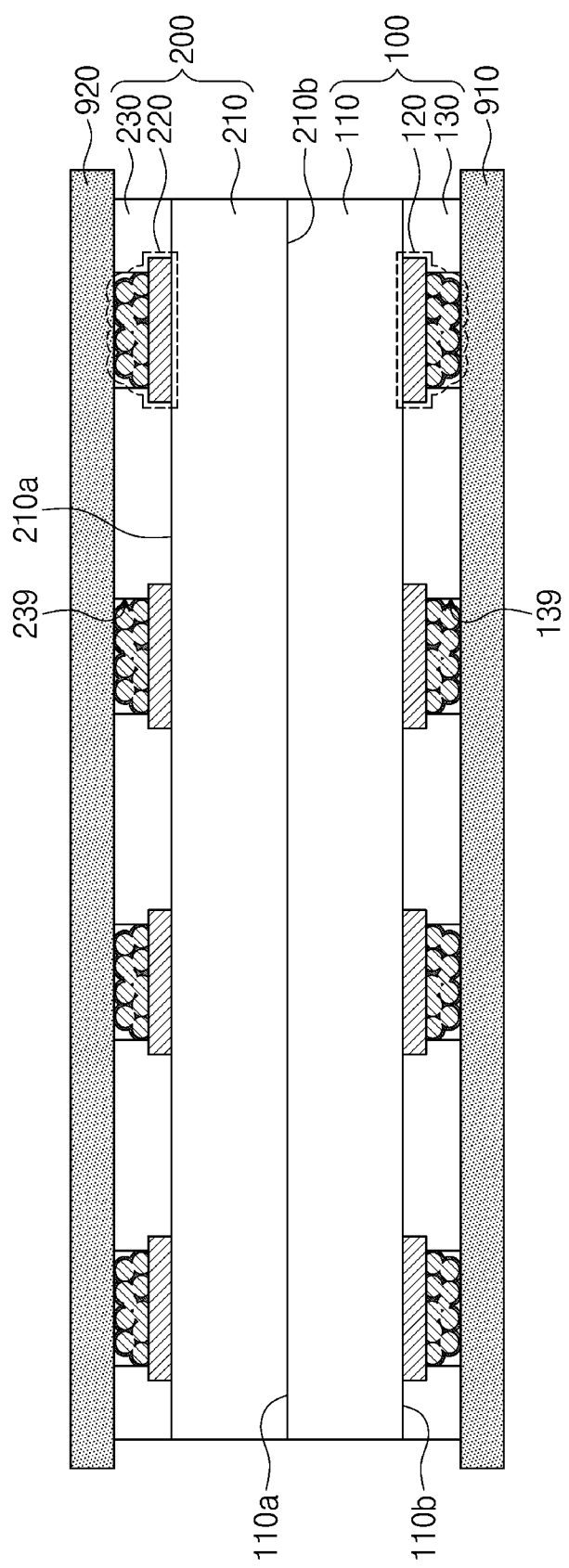

FIGS. 2A to 2C are views for explaining a method for fabricating the sensing device according to an embodiment. Hereinafter, the duplicated descriptions, which have been described already, will be omitted.

Referring to FIG. 2A, a first sensor 100 may be prepared. As described with reference to FIGS. 1A and 1B, the first sensor 100 may include a first substrate 110, first electrodes 120, and a first passivation layer 130. The first electrode 120 and the first passivation layer 130 may be formed on a bottom surface 110b of the first substrate 110. The formation of the first electrode 120 may include formation of a conductive layer (not shown) by thermal deposition or sputtering and patterning of the conductive layer. The patterning of the conductive layer may include formation of a mask layer on the conductive layer and etching of the conductive layer by using the mask layer as an etch mask. A process of forming a first passivation layer 130 may be performed by a coating process or a deposition process. First openings 139 may be formed by a method using laser or a mechanical method. The process of forming the first electrode 120 and the process of forming the first passivation layer 130 may be performed at a temperature less than about 100° C. Thus, the first electrodes 120 may be prevented from being damaged by heat, or damage of the first electrodes 120 due to heat may be reduced.

A first plasma treatment process may be performed on a first surface of the first sensor 100. The first surface of the first sensor 100 may correspond to a top surface 110a of the first substrate 110. For example, the first plasma treatment may be performed by using a plasma gas. The plasma gas may include an argon (Ar) gas, a helium (He) gas, an oxygen gas ($O_2$), a nitrogen gas ($N_2$), air, and/or a fluorine-containing gas. The fluorine-containing gas may include carbon tetrafluoride ($CF_4$). The first plasma treatment may include radio frequency (RF) plasma treatment. When plasma is applied to the fluorine-based polymer, radicals may be formed on a plasma-treated portion of the fluorine-based polymer. Since the first substrate 110 includes the fluorine-based polymer, the first radicals may be formed on a top surface 110a of the first substrate 110 by the first plasma treatment process. Surface roughness of the top surface 110a of the first substrate 110 may increase by the first plasma treatment process. After the first plasma treatment process, the top surface 110a of the first substrate 110 may have a surface roughness greater than that of the bottom surface 110b thereof. For example, after the first plasma treatment process, the top surface 110a of the first substrate 110 may have surface roughness of about 30 nm to about 35 nm.

Referring to FIG. 2B, a second sensor 200 may be prepared. As described with reference to FIGS. 1A and 1C, the second sensor 200 may include a second substrate 210, a second electrode 220, and a second passivation layer 230.

A second plasma treatment process may be performed on a second surface of the second sensor 200 to form second radicals. The second radicals may be formed on the second surface of the second sensor 200. The second surface of the second sensor 200 may correspond to a bottom surface 210b of the second substrate 210. The second plasma treatment process may be performed under the same conditions and methods as those of the first plasma treatment process described with reference to FIG. 2A. Surface roughness of the bottom surface 210b of the second substrate 210 may increase by the second plasma treatment process. The bottom surface 210b of the second substrate 210 may have surface roughness greater than that of the top surface thereof. For example, after the second plasma treatment process, the bottom surface 210b of the second substrate 210 may have surface roughness of about 30 nm to about 35 nm.

Referring to FIG. 2C, a second sensor 200 may be disposed on the first sensor 100 so that a second surface of the second sensor 200 faces a first surface of a first sensor 100. For example, the second substrate 210 may be disposed on the first substrate 110 so that the plasma-treated bottom surface 210b of the second substrate 210 faces the plasma-treated top surface 110a of the first substrate 110. Here, the bottom surface 210b of the second substrate 210 may contact the top surface 110a of the first substrate 110. The second sensor 200 may be disposed on the first sensor 100 after the first plasma treatment process and the second plasma treatment process are performed.

A thermocompression process may be performed on the first sensor 100 and the second sensor 200. The thermocompression process may include a process of respectively providing jigs 910 and 920 on the bottom surface of the first sensor 100 and the top surface of the second sensor 200 and a process of applying a pressure to the first sensor 100 and the second sensor 200 by using the jigs 910 and 920. While the pressure is applied, heat may be applied to the first sensor 100 and the second sensor 200.

Since The first radicals and the second radicals are respectively provided on the top surface 110a of the first substrate 110 and the bottom surface 210b of the second substrate 210, the first radicals may react with the second radicals by the thermocompression process. The chemical bonding may be formed between the bottom surface 110b of the first substrate 110 and the top surface 210a of the second substrate 210 due to the reaction. The bonding between the first substrate 110 and the second substrate 210 may be strong.

The thermocompression process may be performed at a temperature equal to or greater than a glass transition temperature and less than a melting point of the first substrate 110. The thermocompression process may be performed at a temperature equal to or greater than a glass transition temperature and less than a melting point of the second substrate 210. When the thermocompression process is performed at a temperature (for example, less than about 100° C.) less than the glass transition temperature of each of the first substrate 110 and the second substrate 210, it may be difficult to form the chemical bonding between the first substrate 110 and the second substrate 210. When the thermocompression process is performed at a temperature (for example, equal to or greater than about 230° C.) equal to or greater than the melting point of each of the first substrate 110 and the second substrate 210, the first substrate 110 and the second substrate 210 may be damaged. For example, the first electrode 120 and the second electrode 220 may be damaged. According to embodiments, the thermocompression process may be performed at a temperature of about 100° C. to about 230° C. Thus, the chemical bonding may be well formed between the first substrate 110 and the second substrate 210, and the damage of the first sensor 100 and the second sensor 200 may be prevented. Also, the thermocompression process may be performed at high efficiency.

When the thermocompression process is performed at a pressure less than about 5 bar/cm$^2$, it may be difficult to form the chemical bonding between the first substrate 110 and the second substrate 210. When the thermocompression process is performed at a pressure greater than about 10 bar/cm$^2$, the first sensor 100 and the second sensor 200 may be damaged. According to embodiments, the thermocompression process may be performed at a pressure of about 5 bar/cm$^2$ to about 10 bar/cm$^2$. Thus, the chemical bonding may be well formed between the first substrate 110 and the second substrate 210, and the damage of the first sensor 100 and the second sensor 200 may be prevented.

After the thermocompression process, the jigs 910 and 920 may be removed. Thus, the sensing device 1 described with reference to FIGS. 1A to 1C may be completely fabricated. The sensing device 1 may be a neural sensing device.

Figure 3:
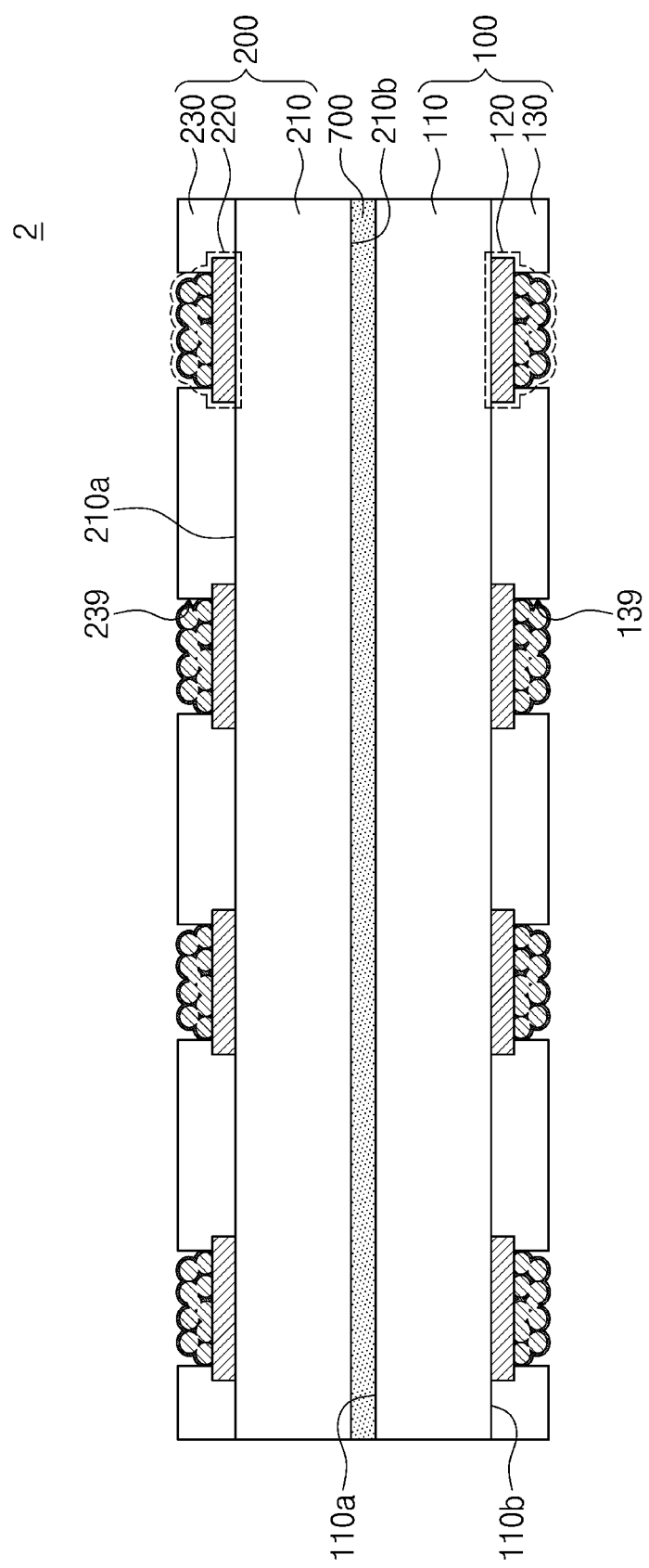
FIG. 3 is a view for explaining a sensing device according to another embodiment.

FIG. 3 is a view for explaining a sensing device according to another embodiment. Hereinafter, the duplicated descriptions, which have been described already, will be omitted.

Referring to FIG. 3, a sensing device 2 may include a first sensor 100, a second sensor 200, and a film 700. As described with reference to FIGS. 1A and 1B, the first sensor 100 may include a first substrate 110, first electrodes 120, and a first passivation layer 130. As described with reference to FIGS. 1A and 1C, the second sensor 200 may include a second substrate 210, second electrodes 220, and a second passivation layer 230.

The film 700 may be disposed between the first sensor 100 and the second sensor 200. The film 700 may include a polymer or a resin. For example, the film 700 may include a crosslinkable polymer. For example, the film 700 may include a photosensitive polymer or a thermally crosslinkable polymer. For example, the film 700 may include a photoresist material and/or perfluoropolyether (PFPE). The photoresist may be, for example, negative photoresist, and the negative photoresist may include epoxy-based negative photoresist such as SU-8. The film 700 may be disposed between a top surface 110a of the first substrate 110 and a bottom surface 210b of the second substrate 210 and then bonded to each of the top surface 110a of the first substrate 110 and the bottom surface 210b of the second substrate 210. For example, the first substrate 110 may be connected to the film 700 through first chemical bonding. The first chemical bonding may be covalent bonding or crosslinked bonding. The second substrate 210 may be connected to the film 700 through second chemical bonding. The second chemical bonding may be covalent bonding or crosslinked bonding. Thus, the second sensor 200 may be bonded to the first sensor 100 through the film 700. The bonding force between the film 700 and the first substrate 110 and the bonding force between the film 700 and the second substrate 210 may be strong. The sensing device 2 may have the improved stability and durability.

Figure 4A:
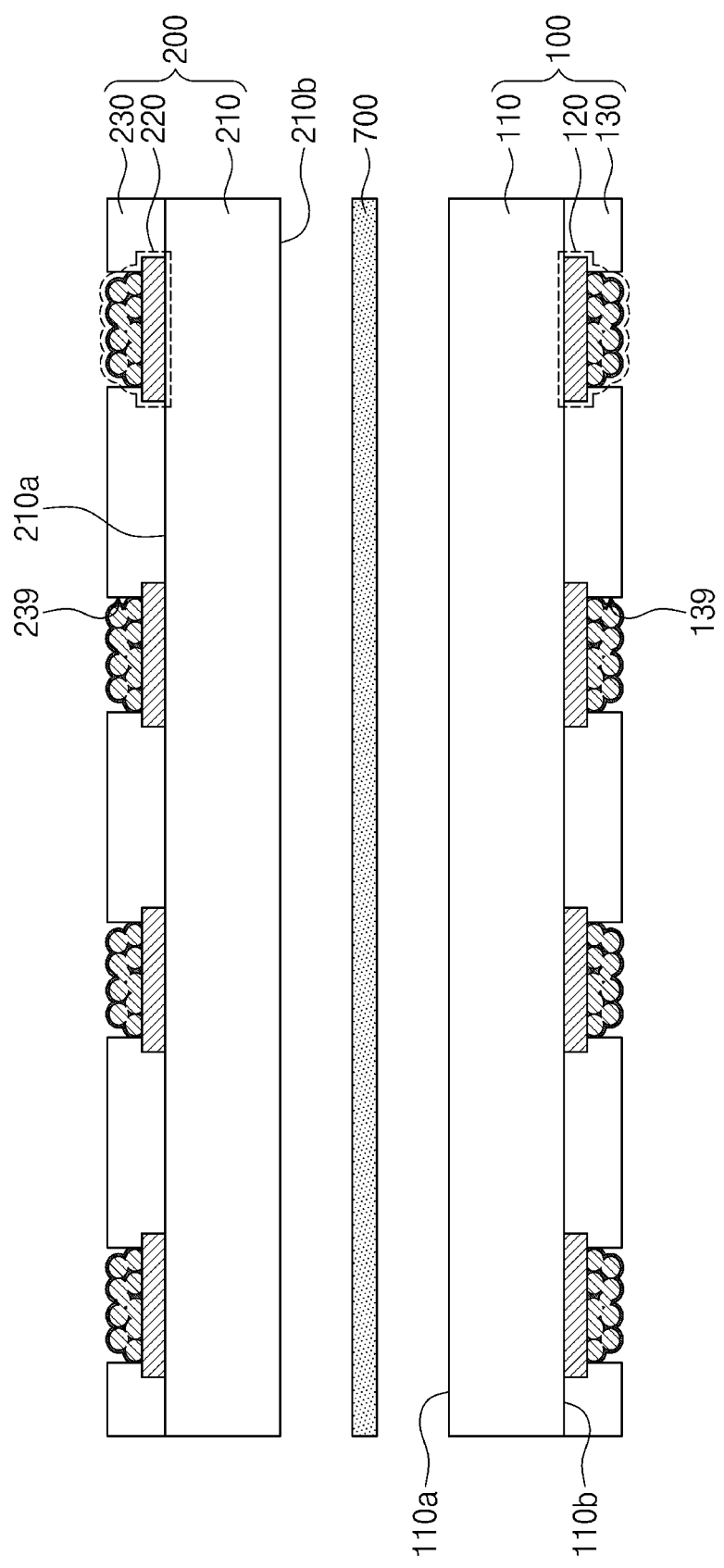
FIGS. 4A and 4B are views for explaining a method for fabricating a sensing device according to another embodiment.
Figure 4B:
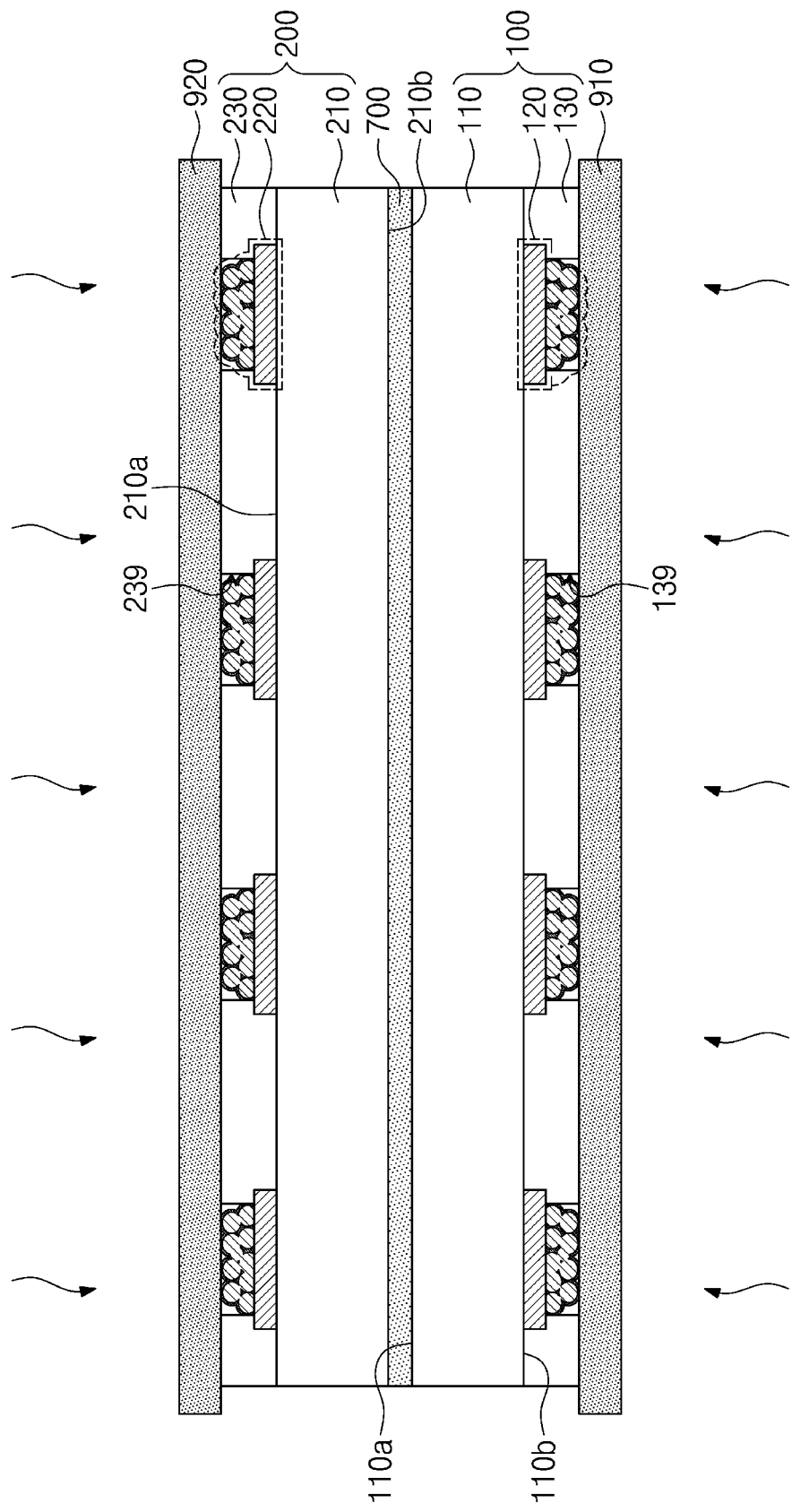

FIGS. 4A and 4B are views for explaining a method for fabricating the sensing device according to another embodiment.

Referring to FIG. 4A, a first sensor 100 may be prepared. A first plasma treatment process may be performed on a top surface 110a of a first substrate 110 to form first radicals on the top surface 110a of the first substrate 110. The first plasma treatment process may be performed under substantially the same method as that of the first plasma treatment process described with reference to FIG. 2A.

A second sensor 200 may be prepared. A second plasma treatment process may be performed on a bottom surface 210b of a second substrate 210 to form second radicals on the bottom surface 210b of the second substrate 210. The second plasma treatment process may be performed under substantially the same method as that of the first plasma treatment process described with reference to FIG. 2B.

The second substrate 210 may be disposed spaced apart from the first substrate 110 so that the plasma-treated bottom surface 210b of the second substrate 210 faces the plasma-treated top surface 110a of the first substrate 110. A film 700 may be disposed between the top surface 100a of the first substrate 110 and a bottom surface 210b of the second substrate 210.

Referring to FIG. 4B, a first jig 910 may be disposed on a bottom surface of a first passivation layer 130, and a second jig 920 may be disposed on a top surface of a second passivation layer 230. The first jig 910 and the second jig 920 may transmit light (for example, ultraviolet rays). The first jig 910 and the second jig 920 may be transparent. The film 700 may contact each of the top surface 100a of the first substrate 110 and the bottom surface 210b of the second substrate 210. Here, the first and second jigs 910 and 920 may be used.

Light or heat may be irradiated onto the top surface of the first sensor 100 and the bottom surface of the second sensor 200. For example, an exposure process may be performed on the first sensor 100 and the second sensor 200. The light may be ultraviolet rays, and the film 700 may include a photosensitive polymer. A chemical structure of the polymers of the film 700 may be changed by the irradiation of the light or heat. The polymers that are changed in chemical structure may react with the radicals. According to embodiments, the film 700 may react with the first radicals on the top surface 110a of the first substrate 100. Thus, first chemical bonding may be formed between the first substrate 110 and the film 700. The film 700 may react with second chemicals on the bottom surface 210b of the second substrate 210. Second chemical bonding may be formed between the second substrate 210 and the film 700.

According to embodiments, the formation of the first and second chemical bonding may be accomplished by changing the chemical structure of the polymer of the film 700 and by a single process. The exposure process may be performed under a low temperature condition. The exposure process may be performed at a temperature less than that of a thermocompression process. The exposure process may be performed at, for example, a temperature of about 10° C. to about 100° C.

After the exposure process, the first jig 910 and the second jig 920 may be transparent. For another example, the first jig 910 and the second jig 930 may not be used during the exposure process. The sensing device 2 described with reference to FIG. 3 may be completely fabricated through the above-described fabrication examples.

Figure 5:
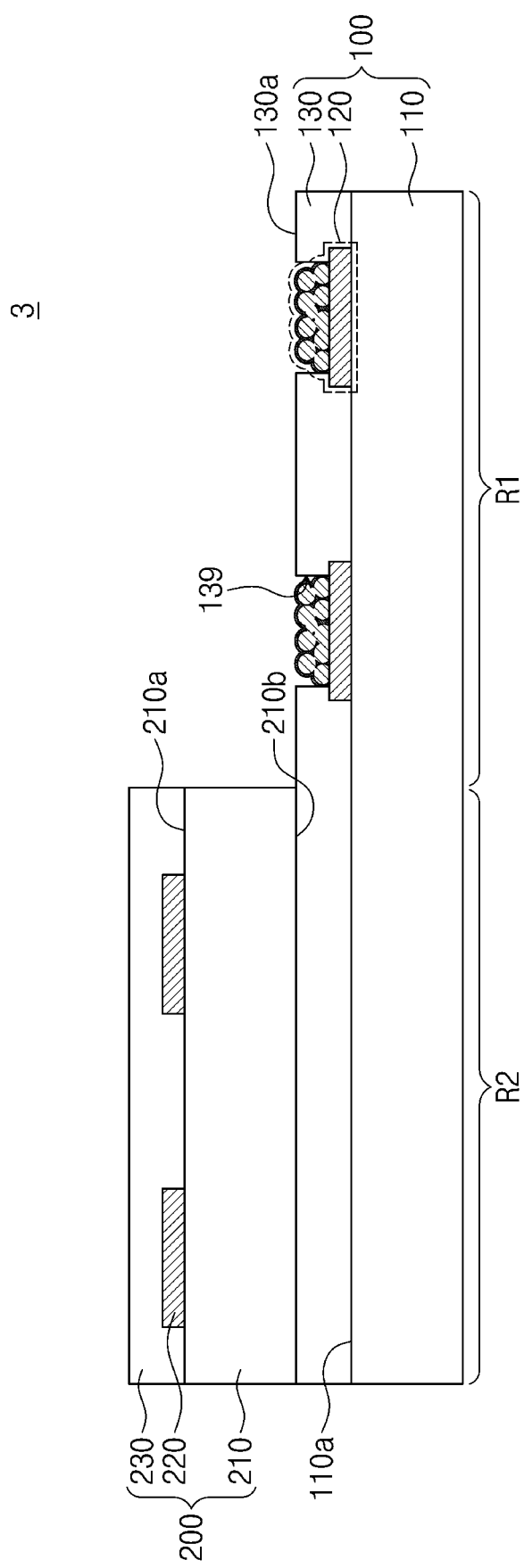
FIG. 5 is a cross-sectional view for explaining a sensing device according to further another embodiment.

FIG. 5 is a cross-sectional view for explaining a sensing device according to further another embodiment.

Referring to FIG. 5, a sensing device 3 may include a first sensor 100 and a second sensor 200. The second sensor 200 may be a sensor that is different from the first sensor 100 to perform a function that is different from that of the first sensor 100. For example, either one of the first sensor 100 and the second sensor 200 may function as a neural electrode sensor, and the other may function as a physical sensor or a chemical sensor. The physical sensor may measure information about a temperature or a pressure. The chemical sensor may measure chemicals or biomaterials such as glucose. Thus, the sensing device 3 may function as a hybrid sensor. Hereinafter, for the simplicity in description of FIG. 5, the first sensor 100 is the neural electrode sensor, and the second sensor 200 is the chemical sensor or the physical sensor, but the embodiments of the inventive concept are not limited thereto. That is, the first sensor 100 may be the chemical sensor or the physical sensor, and the second sensor 200 may be the neural electrode sensor.

As described with reference to FIGS. 1A and 1B, the first sensor 100 may include a first substrate 110, a first electrode 120, and a first passivation layer 130. In view of a plane, the first substrate 110 may have a first area R1 and a second area R2. As illustrated in FIG. 1B, the first electrode may include a first electrode layer 121, a first internal electrode 122, and a first external electrode 123. However, the first electrode 120 and the first passivation layer 130 may be disposed on a top surface 110a of the first substrate 110. The first electrodes 120 may be disposed on the first area R1 of the first substrate 110 but may not be disposed on the second area R2. The first passivation layer 130 may include a fluorine-based polymer. The first passivation layer 130 may cover the first area R1 and the second area R2 of the first substrate 110. The first passivation layer 130 may have a plurality of first openings to expose the first electrodes 120.

The second sensor 200 may have a surface area less than that of the first sensor 100. The second sensor 200 may be disposed on the first sensor 100. For example, the second sensor 200 may be disposed on the second area R2 of the first substrate 110 to expose the first passivation layer 130 and the first electrodes 120 on the first area R1. The second sensor 200 may include a second substrate 210, a second electrode 220, and a second passivation layer 230. The second substrate 210, the second electrode 220, and the second passivation layer 230 may be substantially the same as those of FIG. 1A. However, a bottom surface 210b of the second substrate 210 may physically contact a top surface 130a of the first passivation layer 130. Chemical bonding may be provided between the bottom surface 210b of the second substrate 210 and the first passivation layer 130. Thus, the first sensor 100 and the second sensor 200 may be firmly bonded to each other.

The second sensor 200 may include a plurality of second electrodes 220, and the second electrodes 220 may constitute an electrode array. However, the second electrodes 220 may not include the second internal electrode 222 and the second external electrode 223 of FIG. 1C. A neural signal may be affected by a temperature, a pressure, and/or glucose. When the second sensor 200 is the chemical sensor, the second electrodes may measure biomaterials such as the glucose. In this case, the electrical signals of the first electrodes 120 according to a glucose concentration measured at the second electrodes 220 may be measured/recorded.

When the second sensor 200 is the physical sensor, the second electrodes may measure a temperature or a pressure. In this case, whether the electrical stimulation is applied to the first electrodes 120 and whether the electrical signals are measured/recorded may be controlled according to the temperature or pressure measured at the second electrodes 220.

The second passivation layer 230 may cover top surfaces of the second electrodes 220. Unlike the drawings, the second passivation layer 230 may expose the second electrodes 220.

Figure 6A:
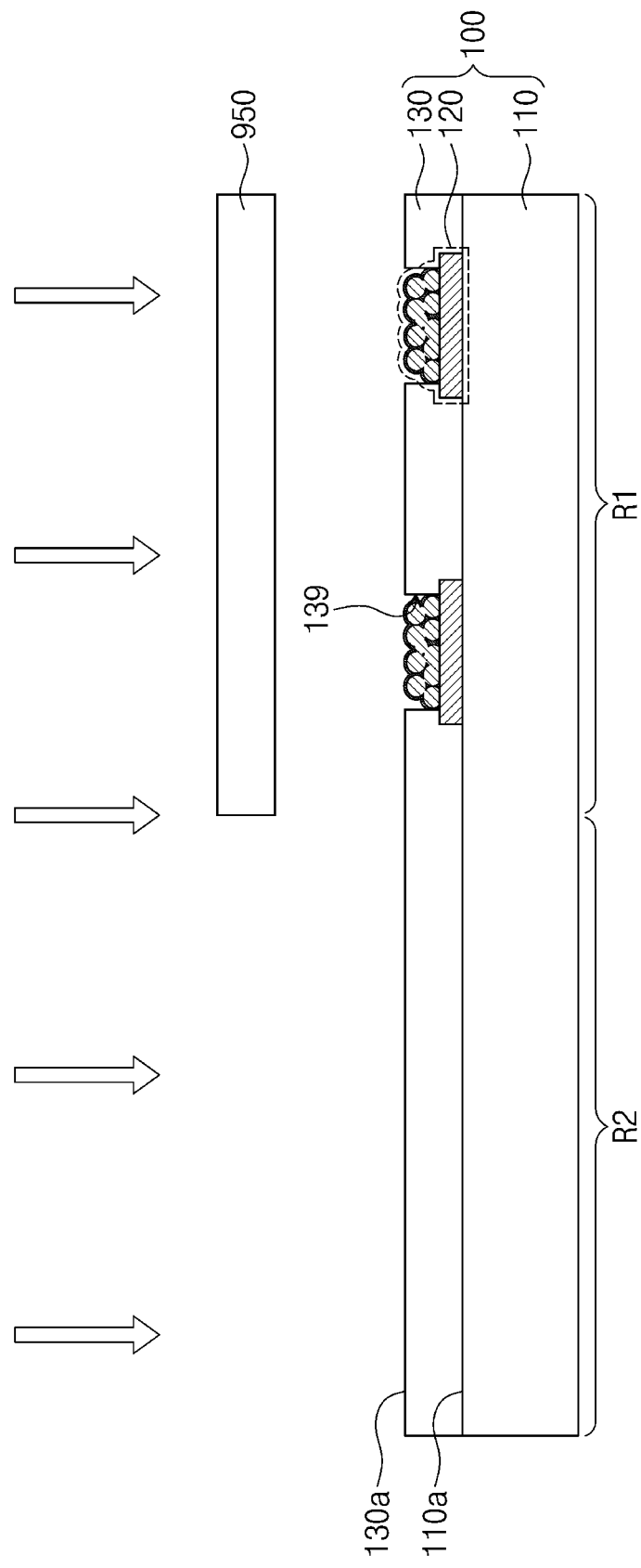
FIGS. 6A to 6C are views for explaining a method for fabricating a sensing device according to further another embodiment.
Figure 6B:
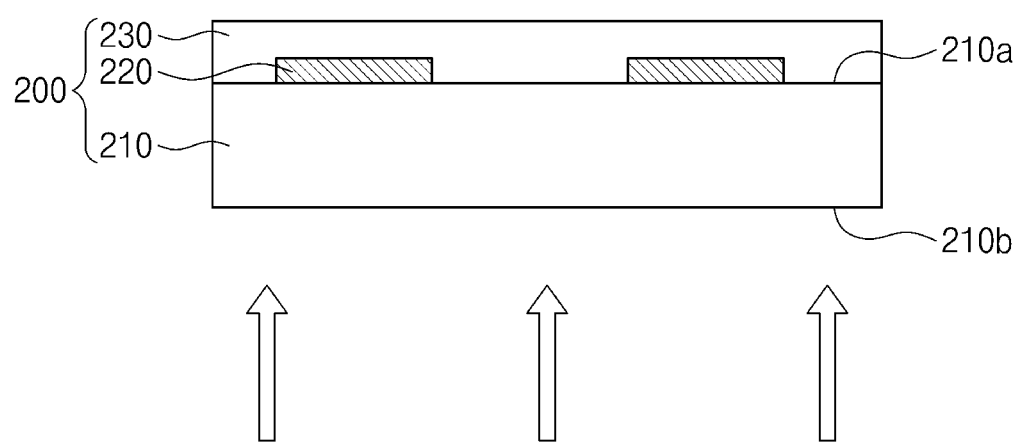
Figure 6C:
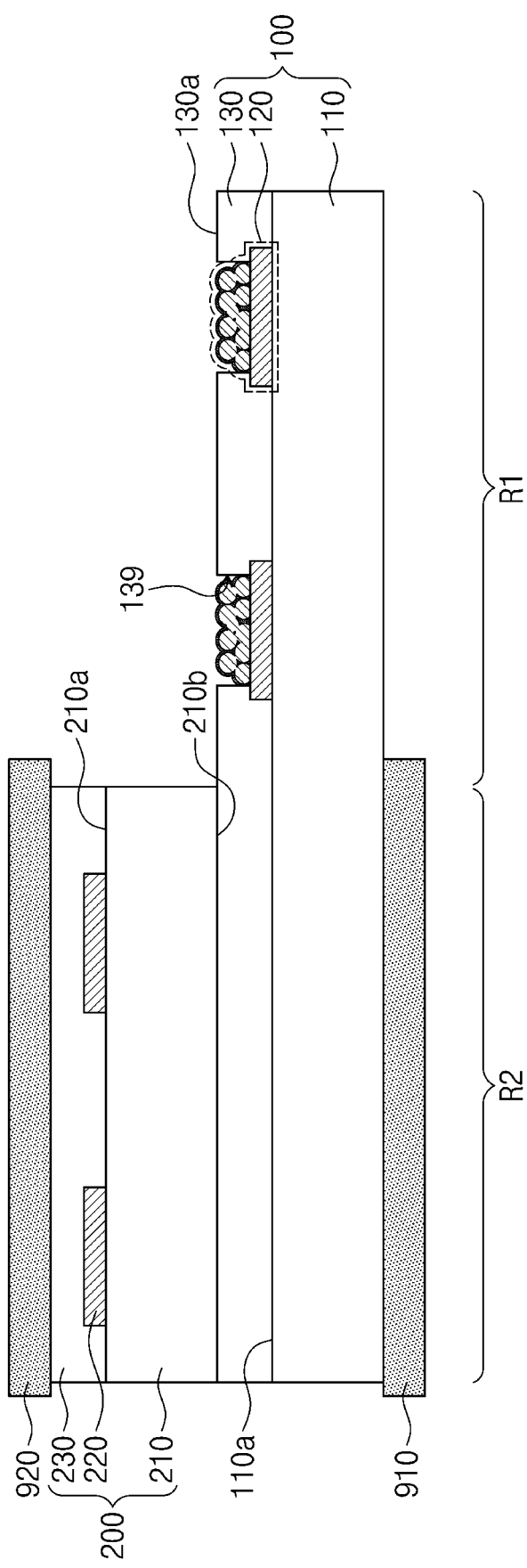

FIGS. 6A to 6C are views for explaining a method for fabricating the sensing device according to an embodiment.

Referring to FIG. 6A, a first sensor 100 may be prepared. As described with reference to FIG. 5, the first sensor 100 may include a first substrate 110, first electrodes 120, and a first passivation layer 130.

A mask 950 may be disposed on the first passivation layer 130 of a first area R1 of the first substrate 110. The mask 950 may expose a top surface 130a of the first passivation layer 130 of a second area R2 of the first substrate 110.

A first plasma treatment process may be performed on a first surface of the first sensor 100 to form first radicals on the first surface of the first sensor 100. The first surface of the first sensor 100 may correspond to a top surface 130a of the first passivation layer 130. Here, the top surface 130a of the first passivation layer 130 on the first area R1 of the first substrate 110 may not be exposed to the first plasma treatment process by the mask 950. First radicals may be formed on the top surface 130a of the first passivation layer 130 of the second area R2 of the first substrate 110 by the first plasma treatment process.

Surface roughness of the top surface 130a of the first passivation layer 130 may increase by the first plasma treatment process. After the first plasma treatment process, the top surface 130a of the first passivation layer 130 of the second area R2 may have surface roughness greater than that of the top surface 130a of the first passivation layer 130 of the first area R1 For example, the top surface 130a of the first passivation layer 130 of the second area R2 may have surface roughness of about 30 nm to about 35 nm. The first plasma treatment process may be performed under the same condition as that of the first plasma treatment process described with reference to FIG. 2A. After the first plasma treatment process, the mask 950 may be removed.

Referring to FIG. 6B, a second sensor 200 may be prepared. As described with reference to FIG. 5, the second sensor 200 may include a second substrate 210, second electrodes 220, and a second passivation layer 230.

A second plasma treatment process may be performed on a second surface of the second sensor 200 to form second radicals. The second surface of the second sensor 200 may correspond to a bottom surface 210b of the second substrate 210. Surface roughness of the bottom surface 210b of the second substrate 210 may increase by the second plasma treatment process. The second plasma treatment process may be performed under the same condition as that of the first plasma treatment process described with reference to FIG. 2B.

Referring to FIG. 6C, a second sensor 200 may be disposed on the first sensor 100 so that a second surface of the second sensor 200 faces a first surface of a first sensor 100. For example, the second substrate 210 may be disposed on the first passivation 130 so that the plasma-treated bottom surface 210b of the second substrate 210 faces the plasma-treated top surface 130a of the first passivation layer 130. The second sensor 200 may overlap the second area R2 of the first substrate 110 in view of a plane.

A thermocompression process may be performed on the first sensor 100 and the second sensor 200. A thermocompression process may be performed under substantially the same condition as that described with reference to FIG. 2C. A first jig 910 and a second jig 920 may be used in the thermocompression process. First radicals may react with second radicals by the thermocompression process. Chemical bonding may be formed between the first passivation layer 130 and the second substrate 210 by the reaction. Thereafter, the jigs 910 and 920 may be removed. The sensing device 3 described with reference to FIG. 5 may be completely fabricated through the above-described fabrication examples.

Figure 7:
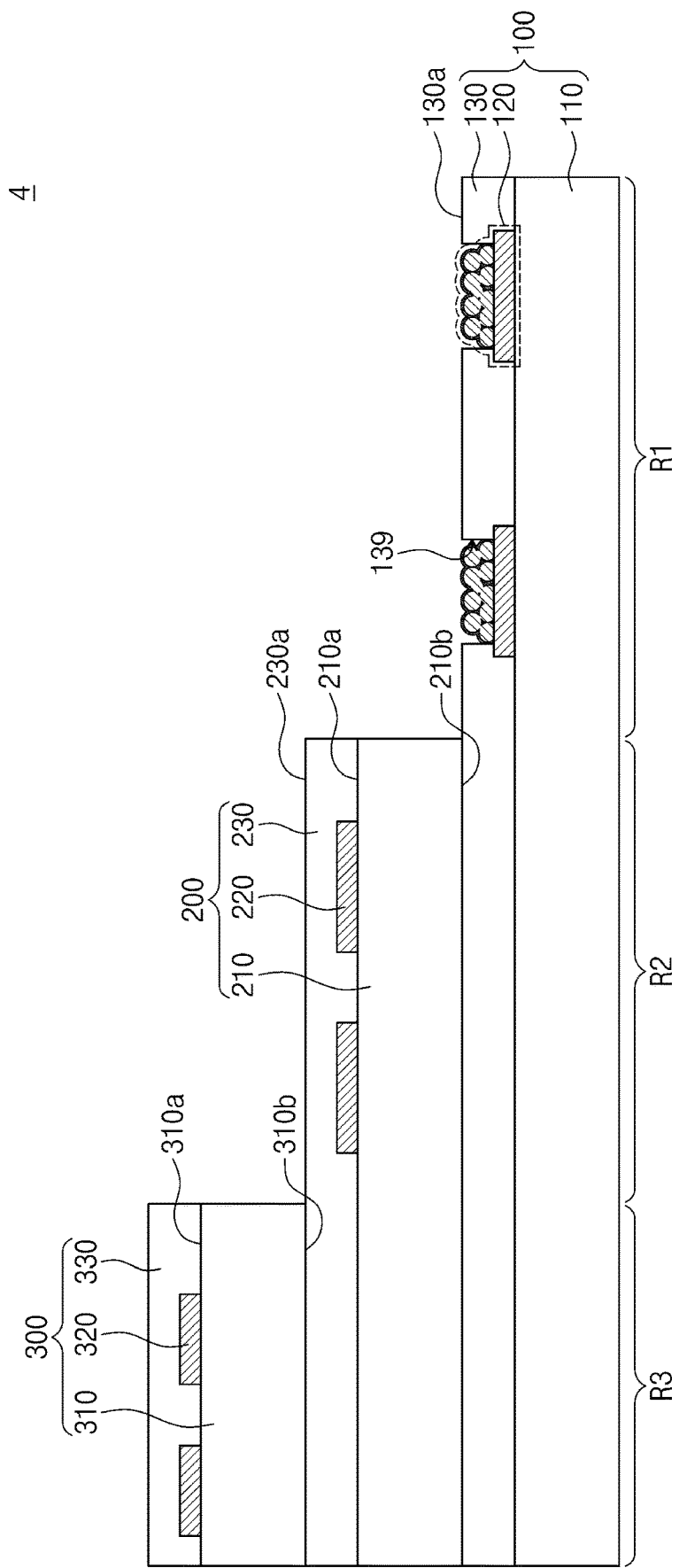
FIG. 7 is a cross-sectional view for explaining a sensing device according to further another embodiment.

FIG. 7 is a cross-sectional view for explaining a sensing device according to further another embodiment.

Referring to FIG. 7, a sensing device 4 may include a first sensor 100, a second sensor 200, and a third sensor 300. The first sensor 100 and the second sensor 200 may be substantially the same as those described with reference to FIG. 5. However, in view of the plane, the first substrate 110 may further include a third area R3 in addition to the first area R1 and the second area R2. The second sensor 200 may overlap the first area R1 and the second area R2 of the first substrate 110 in view of the plane.

The third sensor 300 may be disposed on a top surface of the second sensor 200. The top surface of the second sensor 200 may correspond to a top surface 230a of a second passivation layer 230. The third sensor 300 may overlap the third area of the first substrate 110. The third sensor 300 may include a third substrate 310, third electrodes 320, and a third passivation layer 330. The third substrate 310 may include a fluorine-based polymer. The third substrate 310 may be disposed on the second passivation layer 230. A bottom surface 310b of the third substrate 310 may physically contact the top surface 230a of the second passivation layer 230. The third electrodes 320 may be disposed on a top surface 310a of the third substrate 310. The third electrodes 320 may be arrayed. The third passivation layer 330 may be disposed on the top surface 310a of the third substrate 310. The third passivation layer 330 may further cover top surfaces of the second electrodes 220. Unlike the drawings, the third passivation layer 330 may have third openings that expose the third electrodes 320. Chemical bonding may be provided between the third substrate 310 and the third passivation layer 330.

The third sensor 300 may be connected to the second sensor 200 by fifth chemical bonding. For example, the fifth chemical bonding may be provided between the second passivation layer 230 and the third substrate 310. The second sensor 200 and the third sensor 300 may be firmly bonded to each other by the fifth chemical bonding.

The third sensor 300 may be a sensor that is different from each of the first sensor 100 and the second sensor 200 to perform a function that is different from that of each of the first sensor 100 and the second sensor 200. For example, the first sensor 100 may include a neural electrode sensor, the second sensor 200 may include a chemical sensor, and the third sensor 300 may include a physical sensor. However, the embodiment of the inventive concept is not limited thereto.

Figure 8B:
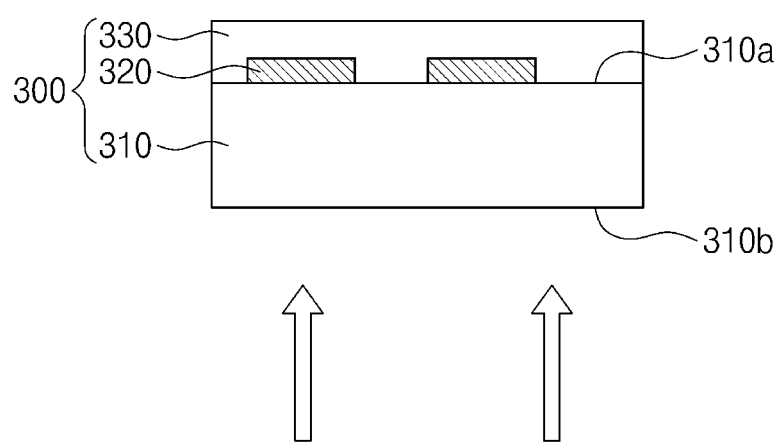
Figure 8C:
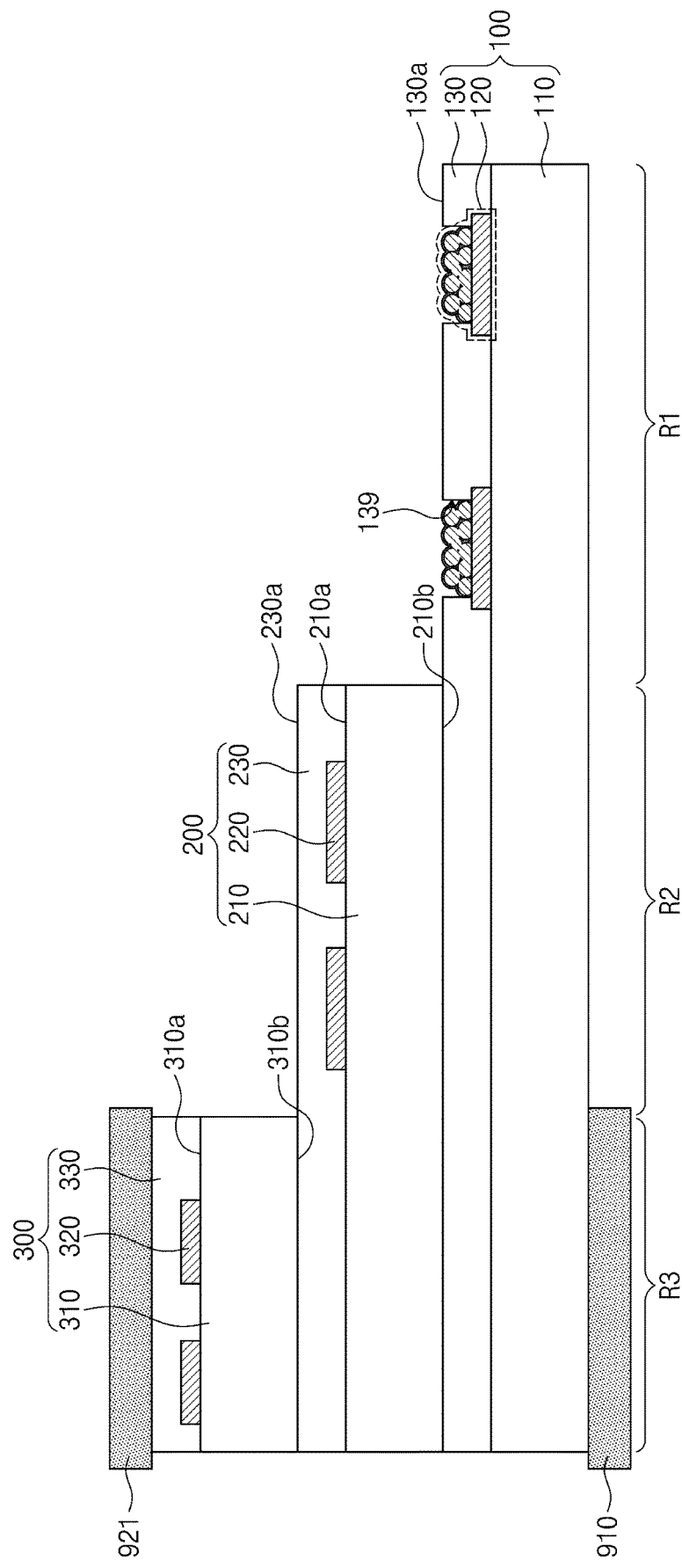

FIGS. 8A to 8C are views for explaining a method for fabricating a sensing device according to an embodiment.

Referring to FIG. 8A, a first sensor 100 and a second sensor 200, which are bonded to each other, may be prepared. The first sensor 100 and the second sensor 200, which are bonded to each other, may be formed through the method described with reference to FIGS. 6A to 6C. The second sensor 200 may be connected to the first sensor through a chemical bonding.

A shadow mask 960 may be disposed on the first sensor 100 and the second sensor 200. The shadow mask 960 may overlap a first area R1 and a second area R2 of the first substrate 110 in view of a plane. The shadow mask 960 may expose a top surface 230a of the second passivation layer 230 of a third area R3 of the first substrate 110.

A third plasma treatment process may be performed on a second surface of the second sensor 200 to form second radicals. A third surface of the second sensor 200 may correspond to the top surface 230a of the second passivation layer 230. Here, a top surface 130a of a first passivation layer 130 and the top surface 230a of the passivation layer 230 of the second area R2 of the second substrate 210 may not be exposed to the third plasma treatment process by the shadow mask 960. Third radicals may be formed on the top surface 230a of the second passivation layer 230 of the third area R3 by the third plasma treatment process. The third plasma treatment process may be performed under the same condition as that of the first plasma treatment process described with reference to FIG. 2A. After the third plasma treatment process, the shadow mask 960 may be removed.

Referring to FIG. 8B, a third sensor 300 may be prepared. The third sensor 300 may include a third substrate 310, third electrodes 320, and a third passivation layer 330.

A fourth plasma treatment process may be performed on a fourth surface of the third sensor 300 to form fourth radicals. The fourth surface of the third sensor 300 may correspond to a bottom surface 310b of the third substrate 310. Surface roughness of the bottom surface 310b of the third substrate 310 may increase by the second plasma treatment process. For example, the bottom surface 310b of the third substrate 310 may have surface roughness of about 30 nm to about 35 nm. The fourth plasma treatment process may be performed under the same condition as that of the first plasma treatment process described with reference to FIG. 2A.

Referring to FIG. 8C, the third sensor 300 may be disposed on the second sensor 200 so that the plasma-treated bottom surface 310b of the third substrate 310 faces the plasma-treated top surface 320a of the second passivation layer 230. Here, the third sensor 300 may overlap a second area R3 of the first substrate 110 in view of a plane.

A thermocompression process may be performed on the first sensor 100, the second sensor 200, and the third sensor 300. A first jig 910 and a second jig 921 may be used in the thermocompression process. A first jig 910 and a second jig 921 may be provided on the bottom surface of the first substrate 110 and a top surface of a third passivation layer 330, respectively. A thermocompression process may be performed under substantially the same condition as that described with reference to FIG. 2C. Third radicals may react with fourth radicals by the thermocompression process. Chemical bonding may be formed between the second passivation layer 230 and the third substrate 310 by the reaction. Thereafter, the jigs 910 and 921 may be removed. The sensing device 4 described with reference to FIG. 7 may be completely fabricated through the above-described fabrication examples.

Figure 9:
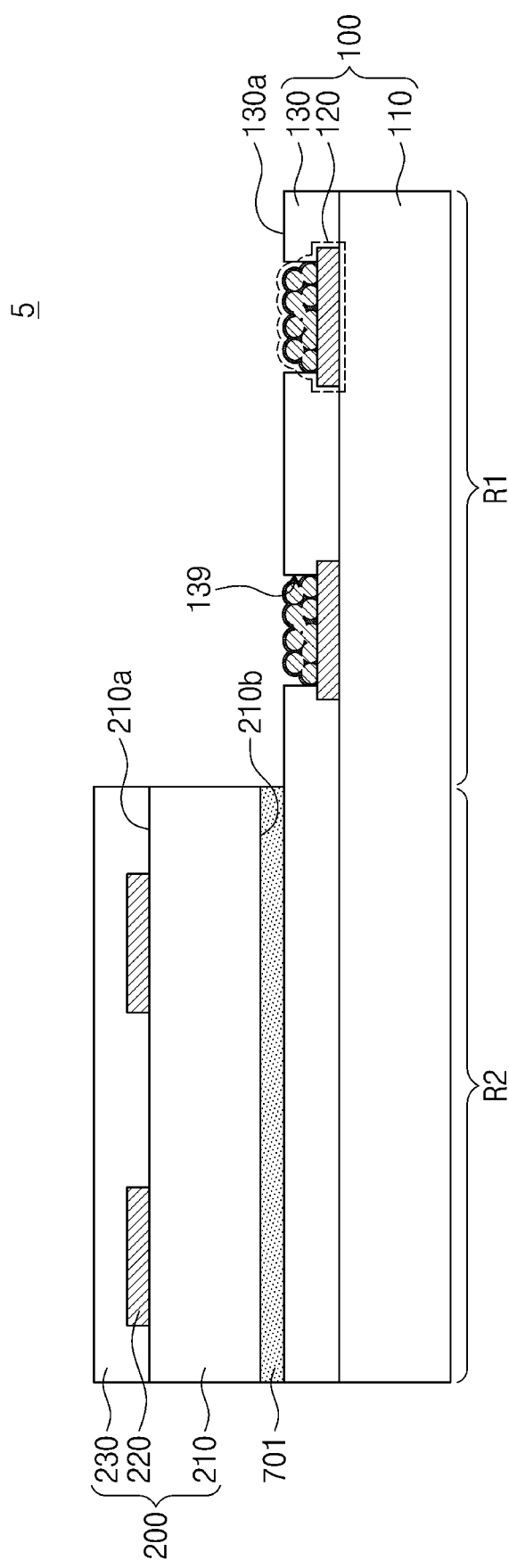
FIG. 9 is a view for explaining a sensing device according to further another embodiment.

FIG. 9 is a view for explaining a sensing device according to further another embodiment. Hereinafter, the duplicated descriptions, which have been described already, will be omitted.

Referring to FIG. 9, a sensing device 5 may include a first sensor 100, a second sensor 200, and a first film 701. The first sensor 100 and the second sensor 200 may be substantially the same as the first sensor 100 and the second sensor 200 of FIG. 5. However, a bottom surface 210b of the second substrate 210 may not contact a top surface of a first passivation layer 130.

The first film 701 may be disposed between the first sensor 100 and the second sensor 200. The first film 701 may be similar to that of the film 700 of FIG. 3, which is described as an example. The film 701 may include a crosslinkable polymer. The first film 701 may be disposed between the top surface 130a of the first passivation layer 130 and a bottom surface 210b of the second substrate 210. For example, the first film 701 may be connected to the first passivation layer 130 through first chemical bonding. The first chemical bonding may be covalent bonding or cross-linked bonding. The second substrate 210 may be connected to the first film 701 through second chemical bonding. The second chemical bonding may be covalent bonding or cross-linked bonding. Thus, the second sensor 200 may be bonded to the first sensor 100 through the first film 701.

Figure 10A:
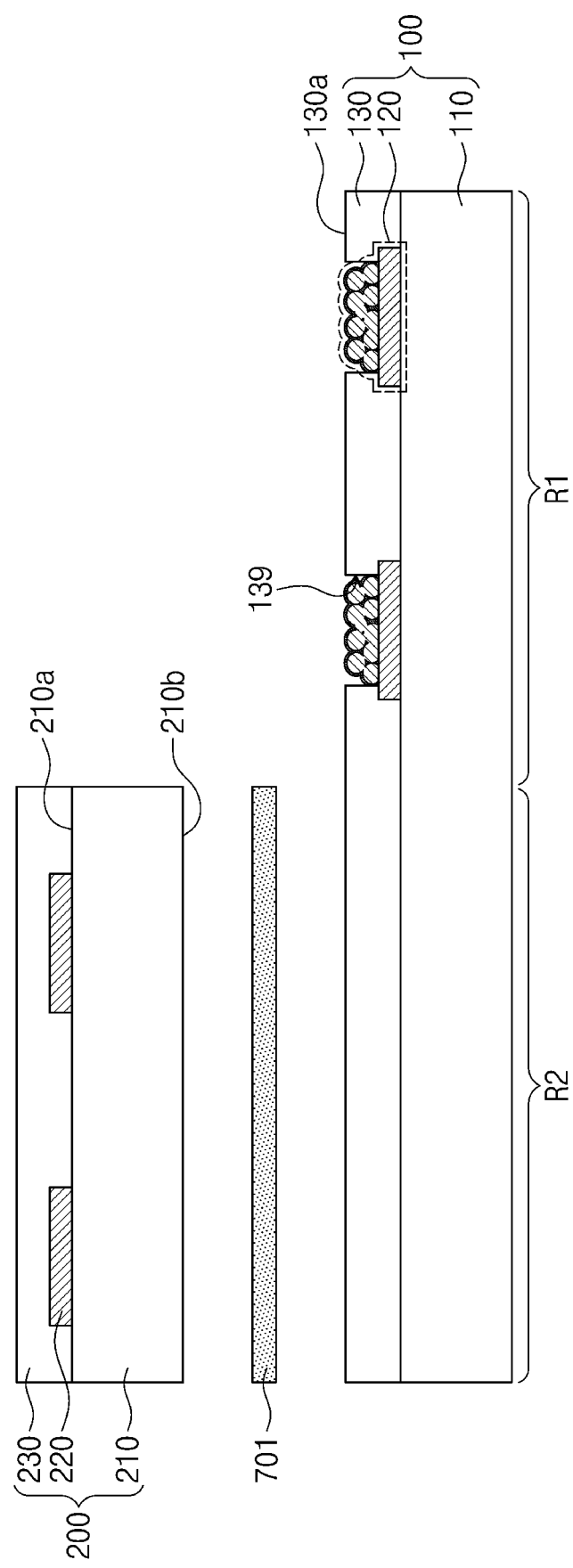

FIGS. 10A and 10B are views for explaining a method for fabricating a sensing device according to further another embodiment.

Referring to FIG. 10A, a first sensor 100 may be prepared. A first plasma treatment process may be performed on a top surface 130a of a first passivation layer 130 to form first radicals. The first plasma treatment process may be performed under substantially the same method as that of the first plasma treatment process described with reference to FIG. 6A.

A second sensor 200 may be prepared. A second plasma treatment process may be performed on a bottom surface 210b of the second substrate 210 to form second radicals. The second plasma treatment process may be performed under substantially the same method as that of the first plasma treatment process described with reference to FIG. 6B.

The second sensor 200 may be disposed on the first sensor 100 so that the plasma-treated bottom surface 210b of the second substrate 210 faces the plasma-treated top surface 130a of the first passivation layer 130. A first film 701 may be disposed between the first passivation layer 130 and the second substrate 210.

Referring to FIG. 10B, light or heat may be irradiated onto the top surface of the first sensor 100 and the bottom surface of the second sensor 200. For example, an exposure process may be performed on the first sensor 100 and the second sensor 200. The light may be ultraviolet rays, and the first film 701 may include a photosensitive polymer. A chemical structure of the polymers of the first film 701 may be changed by the irradiation of the light or heat. Thus, the first film 701 may react with the first radicals on the top surface 130a of the first passivation layer 130 to form first chemical bonding. The first film 701 may react with the second radicals on the bottom surface 210b of the second substrate 210 to form second chemical bonding. An exposure process may be performed under substantially the same method as that described with reference to FIG. 4B. The sensing device 5 described with reference to FIG. 9 may be completely fabricated through the above-described fabrication examples.

Figure 11:
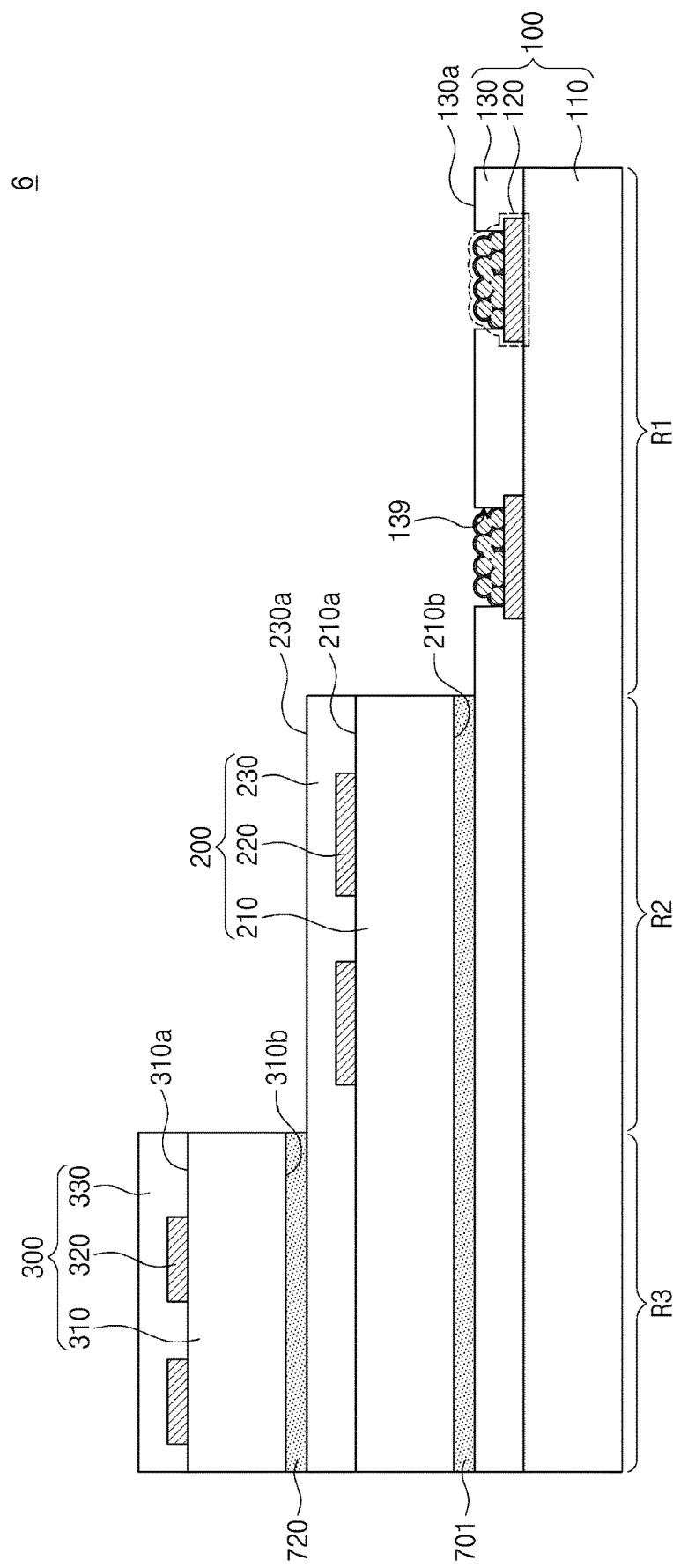
FIG. 11 is a view for explaining a sensing device according to further another embodiment.

FIG. 11 is a view for explaining a sensing device according to further another embodiment. Hereinafter, the duplicated descriptions, which have been described already, will be omitted.

Referring to FIG. 11, a sensing device 6 may include a first sensor 100, a second sensor 200, a third sensor 300, a first film 701, and a second film 720. The first sensor 100, the second sensor 200, and the third sensor 300 may be substantially the same as those described with reference to FIG. 7. However, a bottom surface 310b of a third substrate 310 may not contact a top surface 230a of a second passivation layer 230, and a bottom surface 210b of a second substrate 210 may not contact a top surface 130a of a first passivation layer 130.

The first film 701 may be disposed between the first sensor 100 and the second sensor 200 to contact the first substrate 110 and the second substrate 210. The first film 701 may be substantially the same as the film 701 of FIG. 9. For example, first chemical bonding may be provided between the first film 701 and the first passivation layer 130, and second chemical bonding may be provided between the first film 701 and the second substrate 210.

The second film 720 may be disposed between the second sensor 200 and the third sensor 300 to contact the second passivation layer 230 and the third substrate 310. The second film 720 may include a crosslinkable polymer. For example, the second film 720 may include a photosensitive polymer or a thermally crosslinkable polymer. For example, the second film 720 may include a photoresist material and/or perfluoropolyether (PFPE). The second film 720 may be connected to the second passivation layer 230 through sixth chemical bonding. The sixth chemical bonding may be covalent bonding or crosslinked bonding. The second film 720 may be connected to the third substrate 310 through seventh chemical bonding. The seventh chemical bonding may be covalent bonding or crosslinked bonding. Thus, the third substrate 310 may be firmly bonded to the second passivation layer 230 through the second film 720.

Figure 12:
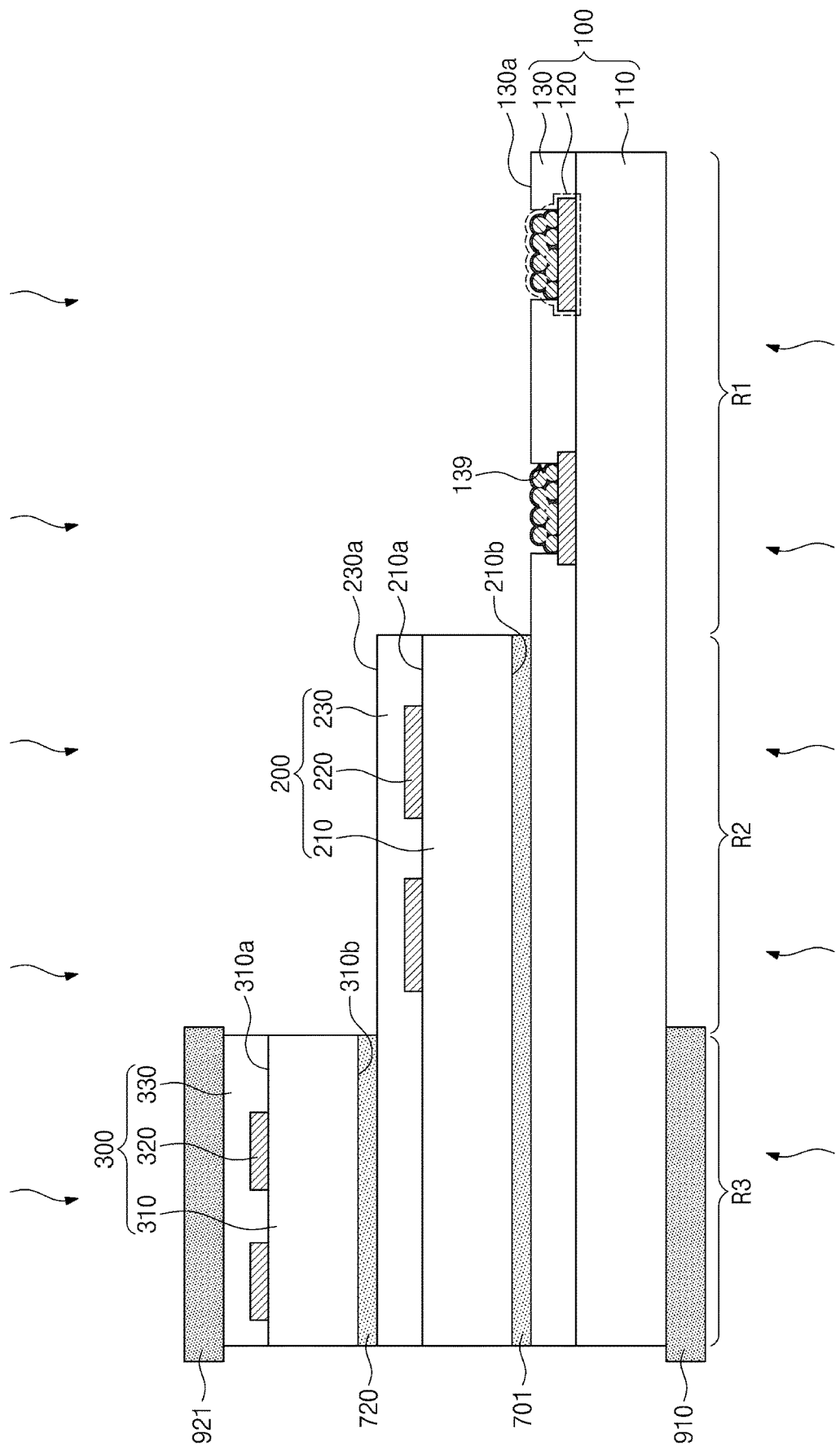
FIG. 12 is a view for explaining a method for fabricating a sensing device according to further another embodiment.

FIG. 12 is a view for explaining a method for fabricating a sensing device according to further another embodiment.

Referring to FIG. 12, a first sensor 100 may be prepared. A first plasma treatment process may be performed on a top surface 130a of a first passivation layer 130 to form first radicals.

A second sensor 200 may be prepared. A second plasma treatment process may be performed on a bottom surface 210b of the second sensor 210 to form second radicals. A third plasma treatment process may be performed on a top surface 230a of a second passivation layer 230 to form third radicals. The third plasma treatment process may be performed under substantially the same condition as that of the first plasma treatment process described with reference to FIG. 8A.

A third sensor 300 may be prepared. A fourth plasma treatment process may be performed on a bottom surface 310b of the third substrate 310 to form fourth radicals.

After the first to fourth plasma treatment processes are ended, the second sensor 200 may be disposed on the first sensor 100 so that the plasma-treated bottom surface 210b of the second substrate 210 faces the plasma-treated top surface 130a of the first passivation layer 130. A first film 701 may be disposed between the first passivation layer 130 and the second substrate 210.

The third sensor 300 may be disposed on the second sensor 200 so that the plasma-treated bottom surface 310b of the third substrate 310 faces the plasma-treated top surface 230a of the second passivation layer 230. Here, a second film 720 may be disposed between the second passivation layer 230 and the third substrate 310.

Referring to FIG. 10B, light or heat may be irradiated onto at least one of the of the first sensor 100 or the third sensor 300. For example, an exposure process may be performed on the bottom surface of the first sensor 100 and the top surface of the third sensor 300. The light may be ultraviolet rays, and each of the first film 701 and the second film 720 may include a photosensitive polymer. A first jig 910 and a second jig 921 may be further used in the exposure process. The first jig 910 and the second jig 921 may transmit light (for example, ultraviolet rays). The first jig 910 and the second jig 921 may be transparent. A chemical structure of each of the polymers of the first film 710 and the second film 720 may be changed by the exposure process. Thus, the first film 701 may react with the first radicals on the top surface 130a of the first passivation layer 130 to form first chemical bonding. The first film 701 may react with the second radicals on the bottom surface 210b of the second substrate 210 to form second chemical bonding. The second film 720 may react with third radicals on the top surface 230a of the second passivation layer 230 to form third chemical bonding. The second film 720 may react with fourth radicals on the bottom surface 310b of the third substrate 310 to form fourth chemical bonding. An exposure process may be performed under substantially the same method as that described with reference to FIG. 4B. According to embodiments, the change in chemical structure of the polymer of the film 700 may be performed by forming the first to fourth chemical bonding and by a single process. After the exposure process, the first jig 910 and the second jig 921 may be transparent. The sensing device 6 described with reference to FIG. 11 may be completely fabricated through the above-described fabrication examples.

Hereinafter, the sensing device, for example, the first sensor 100 and a method for fabricating the same will be described in more detail.

FIGS. 13 to 21 are cross-sectional views for explaining a method of fabricating the sensing device according to an embodiment of the inventive concept.

Figure 13:
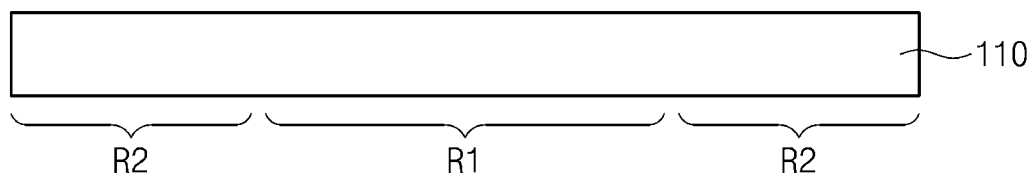
FIGS. 13 to 21 are cross-sectional views for explaining a method of fabricating a sensing device according to an embodiment of the inventive concept.

Referring to FIG. 13, a first substrate 110 may be prepared. In view of a plane, the first substrate 110 may have a first area R1 and a second area R2. The first substrate 110 may include a fluorine-based polymer and have an insulation property. The fluorine-based polymer may be a fluorohydrocarbon polymer and may have a plurality of carbon-fluorine (C—F) bonds. For example, the fluorine-based polymer may include fluorinated ethylene-propylene (FEP), perfluoroalkoxy polymer (PFA), and/or polytetrafluoroethylene (PTFE).

The first substrate 110 may be thermally treated. The first substrate 110 may be thermally treated at a temperature of about 25° C. to about 250° C. During the thermal treatment, a pressure of about 10 bars to 50 bars may be applied to the first substrate 110. Stress of the first substrate 110 may be relaxed by the thermal treatment. For example, stress within the fluorine-based polymer may be relaxed. Thus, contraction of the first substrate 110 may be prevented from being contracted in the process of fabricating the sensing device of FIGS. 14 to 21, which will be described below.

Figure 14:
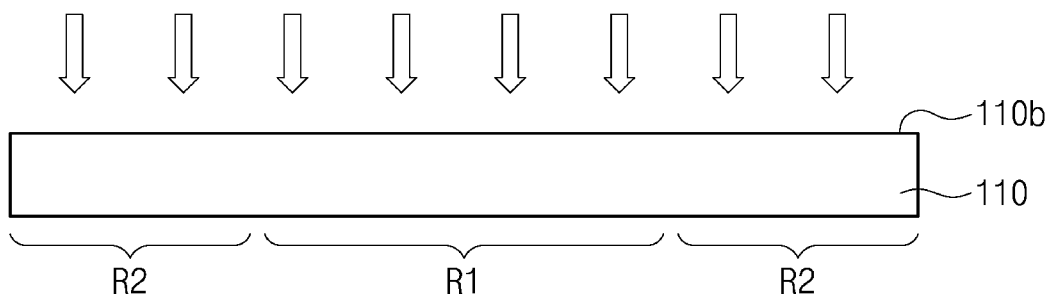

Referring to FIG. 14, a first plasma treatment process may be performed on a first surface 110b of the first sensor 110. For example, the first surface 110b of the first area R1 and the first surface 110b of the second area R2 of the first substrate 110 may be exposed by the first plasma treatment process. The first plasma treatment may be performed by using a plasma gas. The plasma gas may include an argon (Ar) gas, a helium (He) gas, an oxygen gas ($O_2$), a nitrogen gas ($N_2$), air, and/or a fluorine-containing gas. The fluorine-containing gas may include carbon tetrafluoride ($CF_4$). The first plasma treatment may include radio frequency (RF) plasma treatment. When plasma is applied to the fluorine-based polymer, radicals may be formed on the fluorine-based polymer. Since the first substrate 110 includes the fluorine-based polymer, the radicals may be formed on the first surface 110b of the first substrate 110 by the first plasma treatment process. Surface roughness of the first surface 110b of the first substrate 110 may increase by the first plasma treatment process. For example, after the first plasma treatment process, the first surface 110b of the first substrate 110 may have surface roughness of about 30 nm to about 35 nm.

Figure 15:
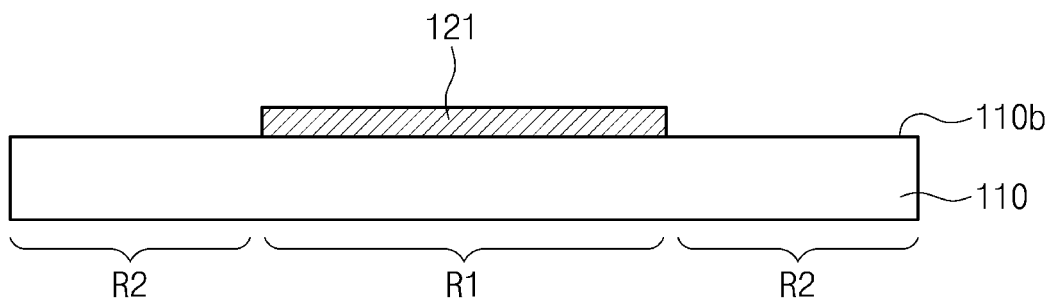

Referring to FIG. 15, a first electrode layer 121 may be formed on the first surface 110b of the first sensor 110. The first surface 110b of the first substrate 110 may correspond to the bottom surface 110b of the first substrate 110, which is previously described with reference to FIGS. 1 to 12. Hereinafter, in description of FIGS. 13 to 22, for convenience of description, the first surface 110b may be called the first surface 110b of the first substrate 110. Furthermore, in the description of FIGS. 13 to 22, the top and bottom will be described with reference to the drawings. For example, a top surface of any component in FIGS. 13 to 22 may be called a bottom surface of the same component in FIGS. 1 to 12. The formation of the first electrode layer 121 may include formation of a conductive layer (not shown) by thermal deposition or sputtering and patterning of the conductive layer. The patterning of the conductive layer may include formation of a mask layer on the conductive layer and etching of the conductive layer by using the mask layer as an etch mask. Thus, the conductive layer exposed by the mask layer may be removed. Etching of the conductive layer may be performed by wet etching. The first electrode layer 121 may cover the first surface 110b of the first area R1 of the first substrate 110 and expose the first surface 110b of the second area R2 of the first substrate 110. The first electrode layer 121 may include a first metal and be provided as a single layer. The first metal may be, for example, gold (Au).

Bonding force between the fluorine-based polymer and the first metal may be relatively weak. When the first plasma treatment process is omitted, bonding force between the first electrode layer and the first surface 110b of the first substrate 110 may be weak. In this case, formation of an adhesion layer between the first electrode layer 121 and the first substrate 110 may be required. The adhesion layer may be a metal bonding layer and may include titanium or chromium. According to embodiments, since the radicals are formed on the first surface 110b of the first substrate 110 by the first plasma processing process of FIG. 14, the bonding force between the first substrate 110 and the first electrode layer 121 may increase. Since the bonding force between the first substrate and the first electrode layer 121 is strong, a separate adhesion layer between the first substrate 110 and the first electrode layer 121 may be omitted. The first electrode layer 121 may directly physically contact the first surface 110b of the first area R1 of the first substrate 110. The adhesion layer may be omitted to simplify the process of fabricating the sensing device and miniaturize the sensing device. Since the bonding force between the first substrate 110 and the first electrode layer 121 increases, the sensing device may be improved in durability.

Figure 16:
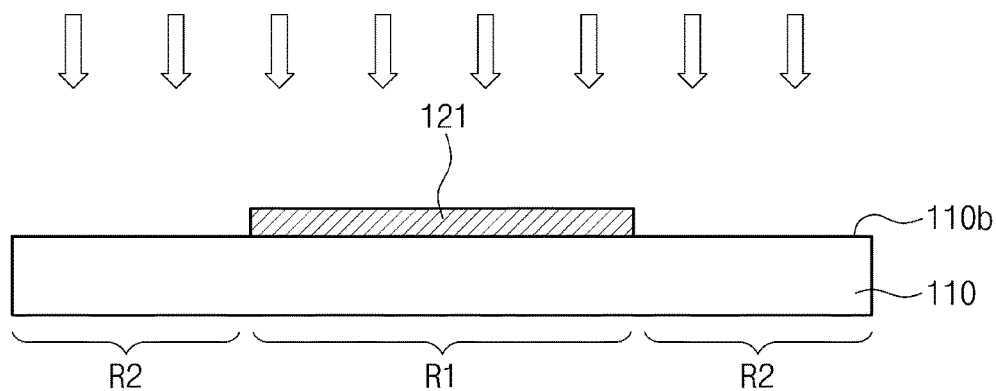

Referring to FIG. 16, a second plasma treatment process may be performed on the first substrate 110 and the first electrode layer 121. The second plasma treatment process may be performed under the same method as that of the first plasma treatment process described with reference to FIG. 14. For example, the second plasma treatment may be performed by using the plasma gas that is described as an example in the first plasma treatment process. The second plasma treatment process may be performed through radio frequency (RF) plasma treatment. The first surface 110b of the second area R2 of the first substrate 110 may be exposed to the second plasma treatment process. The first area R1 of the first substrate 110 may not be exposed to the second plasma treatment process by the first electrode layer 121. The second plasma treatment process may be performed on the second area R2 of the first substrate 110 to generate radicals on the first surface 110b of the second area R2 of the first substrate 110.

Surface roughness of the first surface 110b of the second area R2 of the first substrate 110 may increase by the second plasma treatment process. The surface roughness of the second area R2 of the first substrate 110 may be greater than that of the first surface 110b of the first area R1 of the first substrate 110.

Figure 17:
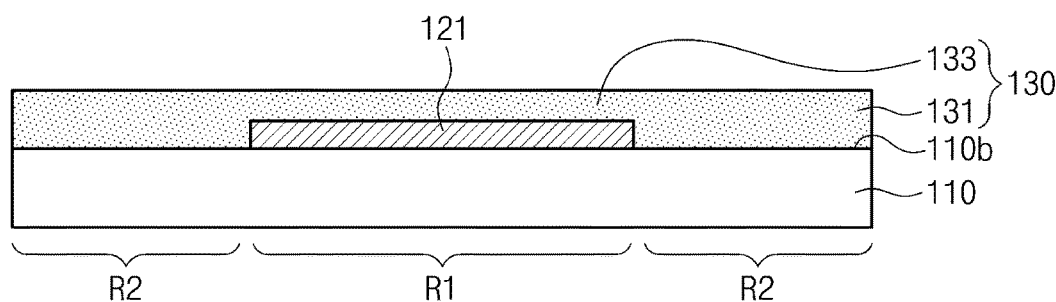

Referring to FIG. 17, a first passivation layer 130 may be formed on the first substrate 110 and the first electrode layer 121 to cover the first surface 110b of the second area R2 of the first substrate 110, a side surface of the first electrode layer 121, and the top surface of the first electrode layer 121. The formation of the first passivation layer may be performed through a spin coating process using a polymer solution. Thereafter, a soft bake process may be performed on the first passivation layer 130. The soft bake process may be performed at a temperature of about 50° C. to about 150° C. The first passivation layer 130 may include photosensitive polymers. The photosensitive polymers may be photocrosslinkable polymers. For example, the first passivation layer 130 may include negative photoresist such as SU-8 and/or perfluoropolyether (PFPE). The SU-8 may be epoxy-based negative photoresist. The first passivation layer 130 may have an insulation property. For example, the photosensitive polymer may include a photosensitive insulating polymer.

The first passivation layer 130 may have a first portion 133 and a second portion 131. The first portion 133 of the first passivation layer 130 may overlap the first area R1 of the first substrate 110 and be disposed on the first surface 110b of the first electrode layer 121. The second portion 131 of the first passivation layer 130 may overlap the second area R2 of the first substrate 110 to physically contact the first surface 110b of the second area R2 of the first substrate 110. The second portion 131 of the first passivation layer 130 may cover a portion of the first surface 110b of the first electrode layer 121. For example, the second portion 131 of the first passivation layer 130 may further cover the first surface 110b of an edge area of the first electrode layer 121. The second portion 131 of the first passivation layer 130 may be connected to the first portion 133 without a boundary.

Figure 18:
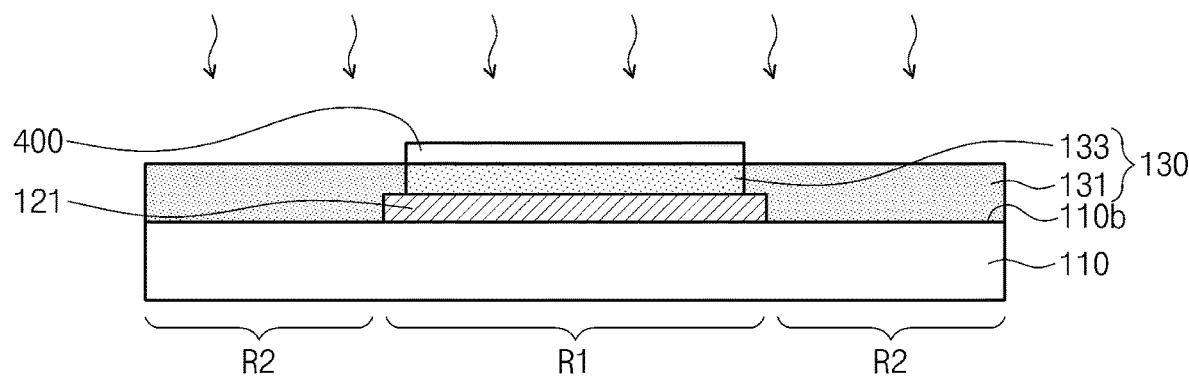

Referring to FIG. 18, the first passivation layer 130 may be formed on a mask pattern 400. The mask pattern 400 may cover the first portion 133 of the first passivation layer 130 and expose the second portion 131. In view of a plane, the mask pattern may overlap the first electrode layer 121. The mask pattern 400 may have a diameter less than that of the first electrode layer 121.

An exposure process may be performed on the first passivation layer 130. For example, light may be irradiated onto the second portion 131 of the first passivation layer 130, which is exposed by the mask pattern 400. The light may be ultraviolet rays. The photosensitive polymers in the second portion 131 of the first passivation layer 130 may be crosslinked with each other by the light. Thus, the photosensitive polymers of the second portion 131 of the first passivation layer 130 may be changed in chemical structure.

During the exposure process, the photosensitive polymer in the second portion 131 of the first passivation layer 130 may react with radicals on the first surface 110b of the second area R2 of the first substrate 110. Thus, chemical bonding may be formed between the second portion 131 of the first passivation layer 130 and the first surface 110b of the second area R2 of the first substrate 110. The chemical bonding may be photocrosslinked bonding.

The radicals may be unstable and may be destroyed when a time elapses. Even through the radicals are formed on the first surface 110b of the second area R2 of the first substrate 110 in the first plasma processing process, after the formation of the first electrode layer 121 of FIG. 15, at least a portion of the radicals may be destroyed. According to embodiments, even though a portion of the radicals on the first surface 110b of the second area R2 of the first substrate 110 is destroyed, radicals may be generated on the first surface 110b of the second area R2 of the first substrate 110 by the second plasma treatment process. Thus, the good chemical bonding may be formed between the second portion 131 of the first passivation layer 130 and the first surface 110b of the second area R2 of the first substrate 110. The first passivation layer 130 may be sufficiently strongly bonded to the first substrate 110 by the chemical bonding.

According to embodiments, the formation of the chemical bonding between the first substrate 110 and the first passivation layer 130 may be accomplished by changing the chemical structure of the second portion 131 of the first passivation layer 130 and by a single process. For example, the chemical bonding may be formed between the first substrate 110 and the first passivation layer 130 in the exposure process for patterning the first passivation layer 130. Thus, a separate process (e.g., a thermocompression process) for forming the chemical bonding between the first substrate 110 and the first passivation layer 130 may be omitted. Thus, the process of fabricating the sensing device may be simplified.

When the chemical bonding is formed between the first substrate 110 and the first passivation layer 130 by the thermocompression process, the thermocompression process may be performed at a temperature of about 200° C. or more. The first passivation layer 130 or the first substrate 110 may be damaged under the temperature condition. According to embodiments, since the chemical bonding is formed between the first substrate 110 and the first passivation layer 130 in the exposure process, the thermocompression process may be omitted on the first passivation layer 130. The exposure process may be performed under a low temperature condition. For example, the exposure process may be performed at a temperature less than that of a thermocompression process. The exposure process may be performed at, for example, a temperature of about 10° C. to about 100° C. Thus, the first substrate 110 and the first passivation layer 130 may be prevented from being damaged. Thereafter, the mask pattern 400 may be removed.

Figure 19:
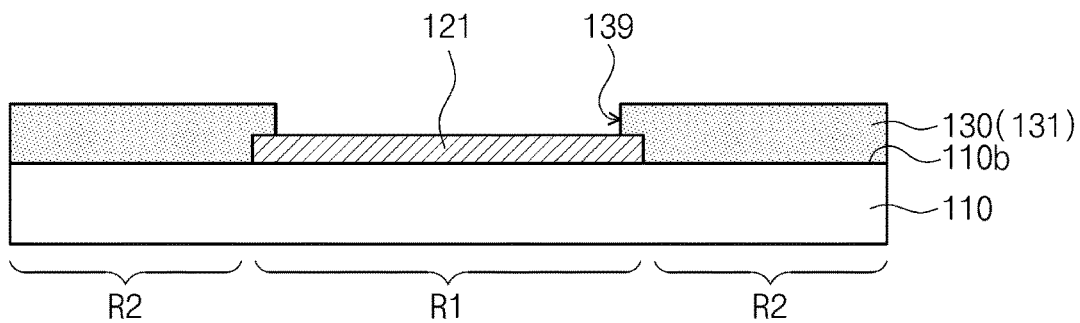

Referring to FIG. 19, a development process may be performed on the first passivation layer 130 to form a first opening 139. The first portion 133 of the first passivation layer 130 may be removed by a developer to form the first opening 139. The first opening 139 may be formed in the first passivation layer 130 to expose the first electrode layer 121. The chemical structure of the second portion 131 of the first passivation layer 130 may have low reactivity with respect to the developer. After the development process, the second portion 131 of the first passivation layer 130 may remain.

Figure 20:
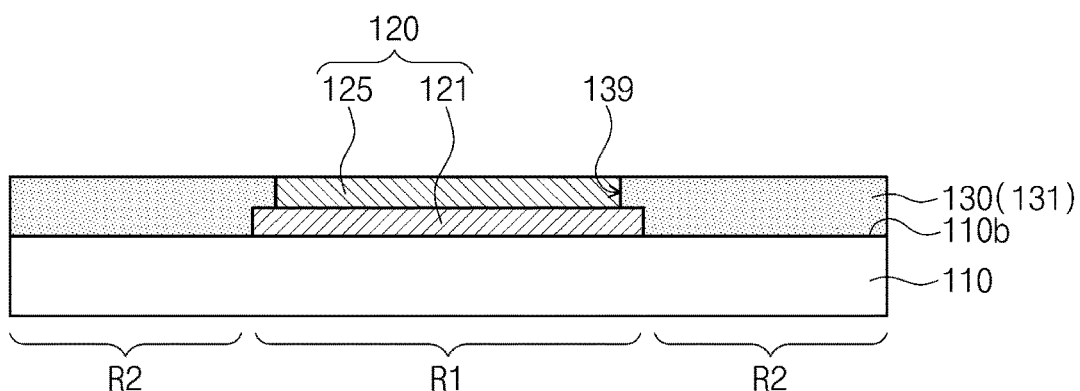

Referring to FIG. 20, a preliminary electrode layer 125 may be formed on the first electrode layer 121 and in the first opening 139. The preliminary electrode layer 125 may be formed by an electro-deposition process. The preliminary electrode layer 125 may include a first metal and a third metal. The third metal may be different from the first metal. For another example, the preliminary electrode layer 125 may include a first metal, a second metal, and a third metal. The first metal may include gold (Au), the second metal may include platinum (Pt), and the third metal may include silver (Ag).

Figure 21:
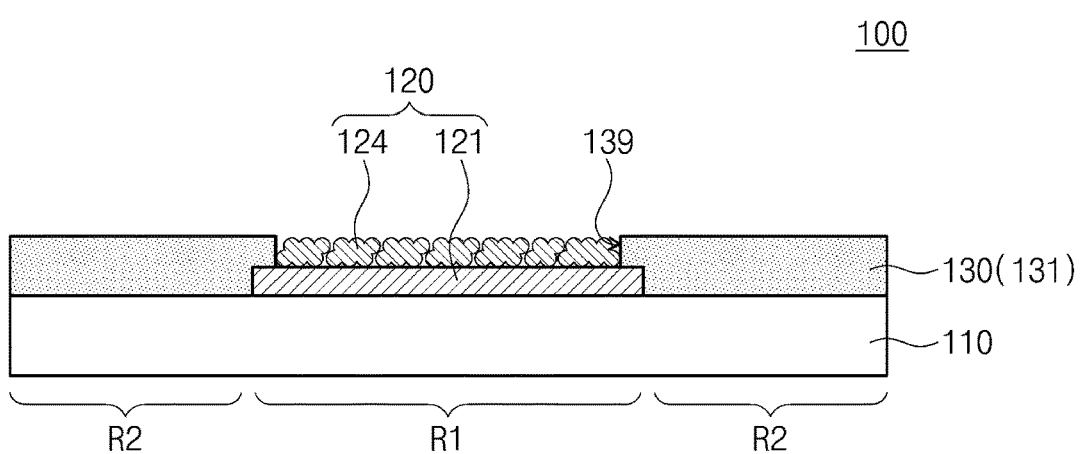

Referring to FIG. 21, the upper electrode 124 may be formed by applying a treatment solution on the preliminary electrode layer 125. The treatment solution may include acid such as a concentrated nitric acid solution. A content of nitric acid in the concentrated nitric acid solution may be about 40% to about 80%, specifically, about 60%. The treatment solution may react with the second metal of the preliminary electrode layer 125. The second metal of the preliminary electrode layer 125 may be removed by the above-described reaction.

The treatment solution is prepared at a relatively high temperature and then applied on the preliminary electrode layer 125. The temperature may be about 50° C. to 100° C., specifically, about 70° C. Since the temperature of the applied treatment solution is high, a reaction rate of the treatment solution and the second metal of the preliminary electrode layer 125 may increase. Thus, an upper electrode 124 may be quickly formed.

The second metal may be removed from the preliminary electrode layer 125 to form the upper electrode 124. The upper electrode 124 may be a porous structure. For example, the upper electrode 124 may have pores therein. Thus, the upper electrode 124 may have a density less than that of the first electrode layer 121. The pores may be portions of the third metal of the preliminary electrode layer 125, which are removed by the reaction with the treatment solution. The first and second metals of the preliminary electrode layer 125 may remain due to the low reactivity with respect to the treatment solution. The first metal of the remaining preliminary electrode layer 125 may form the upper electrode 124. The upper electrode 124 may include the same material as the first electrode layer 121 (e.g., the first metal). The upper electrode 124 may further include a second metal. The upper electrode 124 may include gold (Au) or a gold-platinum (AuPt) alloy.

The first electrode layer 121 may not include the second metal (e.g., silver) so as not to change the porous structure. Thus, an electrode structure 120 may be fabricated. The electrode structure 120 may be the first electrode that is previously described with reference to FIGS. 1 to 13. The electrode structure 120 may include a first electrode layer 121 and an upper electrode 124. The upper electrode 124 may be electrically connected to the first electrode layer 121. According to embodiments, the upper electrode 124 may have the porous structure to easily adjust an impedance of the electrode structure 120. A sensor 100 may be completely fabricated according to the fabrication examples described so far. The sensor 100 may be the first sensor described with reference to FIGS. 1 to 12.

Since bonding force between the first electrode layer 121 and the first substrate 110 and bonding force between the first passivation layer 130 and the first substrate 110 are strong, the sensor 100 may have durability and stability. Thus, the sensor 100 may be inserted into a human body or attached to a living body and thus be used without side effects.

According to embodiments, since the thermocompression process is omitted, the process of fabricating the sensor 100 may be performed at a low temperature. For example, the sensor 100 may be fabricated at a temperature of about 10° C. to about 100° C. Thus, components of the sensor 100 may be prevented from being damaged by heat while the sensor 100 is fabricated. The components of the sensor 100 may include a first substrate 110, an electrode structure 120, and a first passivation layer 130.

According to embodiments, the first substrate 110 and the first passivation layer 130 may have high durability against chemicals. The chemicals may include a strong acid or a strong base. The sensor 100 may be used in various environments. For example, the sensor 100 may be used in the presence of the chemicals. The sensor 100 may be a neural sensor or a neural electrode. The neural electrode may be a neural sensing electrode.

Figure 22:
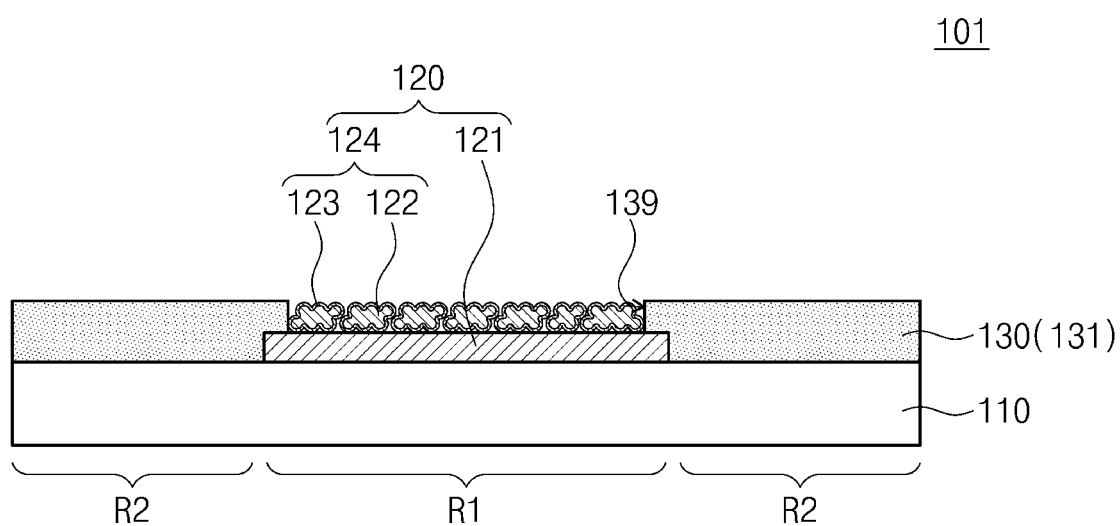
FIG. 22 is a view for explaining a sensing device according to another embodiment.

FIG. 22 is a view for explaining a sensing device according to another embodiment.

Referring to FIG. 22, a sensing device 101 may include a first substrate 110, a first electrode layer 121, an upper electrode 124, and a first passivation layer 130. The first substrate 110, the first electrode layer 121, the upper electrode 124, and the first passivation layer 130 may be fabricated by substantially the same method as described with reference to FIGS. 13 to 21. The upper electrode 124 may have a porous structure.

However, the upper electrode 124 may include an internal electrode 122 and an external electrode 123. The internal electrode may correspond to a core portion of the upper electrode 124. As illustrated in FIGS. 20 and 21, formation of the internal electrode 122 may include formation of the preliminary electrode layer 125 and the removal of the second metal from the preliminary electrode layer 125. The internal electrode 122 may have a porous structure and include the same material as the first electrode layer 121. The internal electrode 122 may include a gold (Au)-containing material. For example, the internal electrode 122 may include gold (Au) or a gold-platinum (AuPt) alloy.

The external electrode 123 may be disposed on the internal electrode 122 to cover a surface of the internal electrode 122. The external electrode may be applied on the internal electrode 122. The external electrode 123 may include a fourth metal, and the fourth metal may be different from the first metal, the second metal, and the third metal. The fourth metal may include iridium (Ir). The upper electrode 124 further includes the external electrode 123 to more improve electrical characteristics of the sensing device 101.

Hereinafter, a method for fabricating the sensing device and an evaluation results of the sensing device using the method will be described with reference to Experimental Examples and Comparative Examples of the inventive concept.

Comparative Example

A flexible substrate is prepared. A first electrode layer is formed on the substrate by using gold (Au). A passivation layer is formed on the substrate by using SU-8. A first opening is formed in the passivation layer. The first electrode layer was fabricated to have an inner diameter of about 100 μm. A separate upper electrode is not formed.

Experimental Example 1

A first electrode layer, a passivation layer, and an upper electrode are formed through the same method as that according to Comparative Example. However, the upper electrode is fabricated by using a gold-platinum (AuPt) alloy.

Experimental Example 2

A first electrode layer, a passivation layer, and an upper electrode are formed through the same method as that according to Comparative Example. However, the internal electrode is formed by using a gold-platinum (AuPt) alloy. iridium (Ir) is applied on the internal electrode to form an external electrode. The upper electrode includes the internal electrode and the external electrode.

Figure 23:
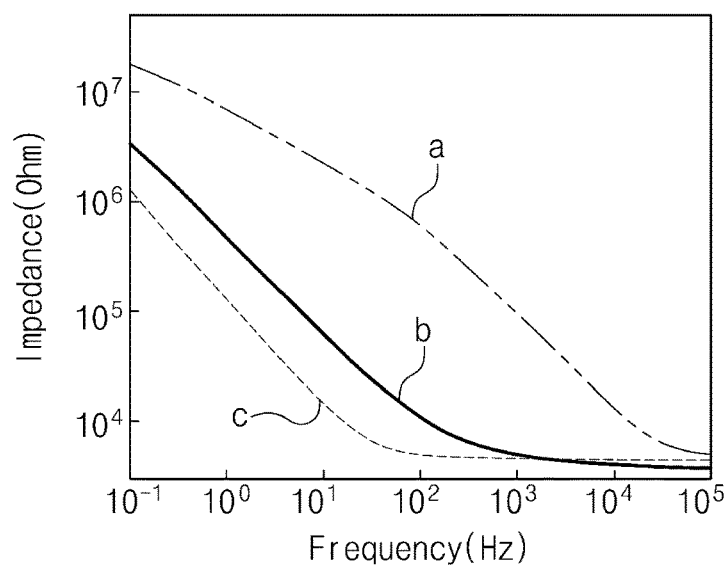
FIG. 23 is a graph showing results obtained by measuring impedances according to Comparative Example, Experimental Example 1, and Experimental Example 2.

FIG. 23 is a graph showing results obtained by measuring impedances according to Comparative Example, Experimental Example 1, and Experimental Example 2. An X-axis represents a frequency, and a y-axis represents an impedance.

Table 1 shows results of analyzing the impedances of Comparative Example, Experimental Example 1, and Experimental Example 2 from the graph of FIG. 23.

TABLE 1

|  | Comparative Example | Experimental Example 1 | Experimental Example 2 |
| --- | --- | --- | --- |
| Impedance (kOhm) | 95.0 | 5.1 | 4.5 |

Referring to FIG. 23 and Table 1, Experimental Example 1(b) and Experimental Example 2(c) show an impedance less than that of Comparative Example (a). As the impedance of the sensing device decreases, sensing noise may be reduced in the sensing process using the electrode. As the sensing noise is reduced, a sensing range of the sensing device may increase. According to embodiments, the upper electrode may include the gold-platinum (AuPt) alloy to improve the sensing range of the sensing device.

Figure 24:
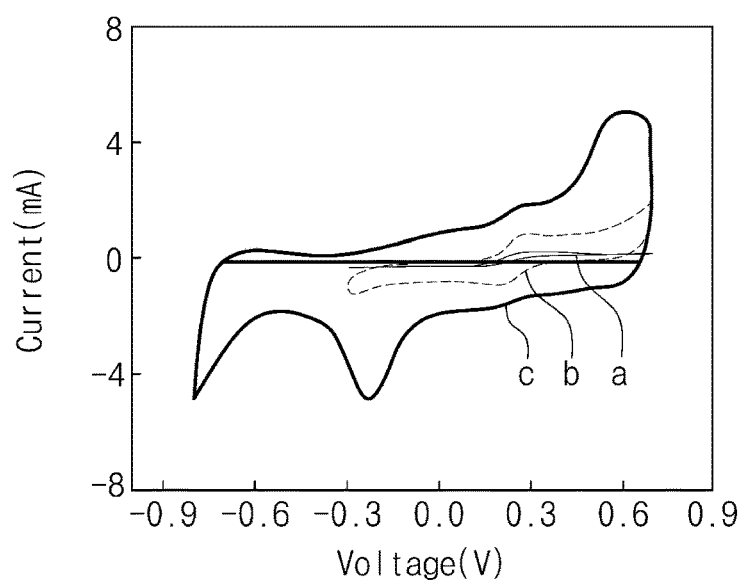
FIG. 24 is a graph showing results of evaluation using a cyclic voltammetry (CV) method according to Comparative Example, Experimental Example 1, and Experimental Example 2.

FIG. 24 is a graph showing results of evaluation using a cyclic voltammetry (CV) method according to Comparative Example, Experimental Example 1, and Experimental Example 2.

Table 2 shows results of analyzing charge storage capacities of Comparative Examples, Experimental Examples 1 and 2 from the graph of FIG. 24.

TABLE 2

|  | Comparative Example | Experimental Example 1 | Experimental Example 2 |
| --- | --- | --- | --- |
| Charge storage capacity (mC/Cm$^2$) | 0.02 | 0.47 | 3.08 |

Referring to FIG. 24 and Table 2, it may be seen that the charge storage capacity of Experimental Example 1(b) and the charge storage capacity of Experimental Example 2(c) are greater than the charge storage capacity of Comparative Example (a). As the charge storage capacity of the sensing device increases, a degree of damage of a sensing target in the sensing process using the sensing device may be reduced. The sensing target may be a neural tissue. The sensing device according to the embodiments has a high charge storage capacity, and thus, the sensing range of the sensing device may be improved.

Figure 25:
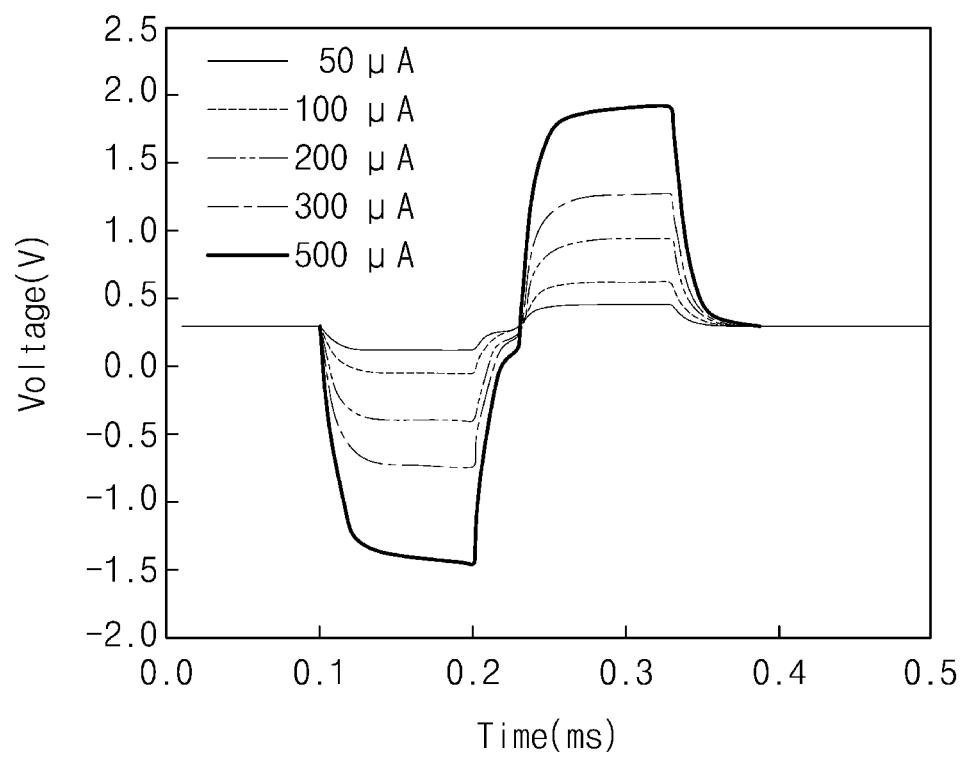
FIG. 25 is a graph showing results obtained by measuring a time-varying voltage according to Experimental Example 2.

FIG. 25 is a graph showing results obtained by measuring a time-varying voltage according to Experimental Example 2. A time delay was 100 μs.

Table 3 shows results of calculating a charge injection limit of Experimental Example 2 from the graph of FIG. 23.

TABLE 3

|  | Experimental Example 2 |
| --- | --- |
| Charge injection limit (mC) | 0.55 |

The charge injection limit of Experimental Example 2 was analyzed to be about 0.55 mC. The more a charge injection limit value of the sensing device increases (for example, about 0.5 mC or more), the more the sensing device may effectively stimulate the target. The target may be a neural tissue. Experimental Example 2 has a charge injection limit of about 0.55 mC, and thus, the sensing device may effectively stimulate the target.

According to the embodiments of the inventive concept, the second sensor may be directly or indirectly bonded to the first sensor by the chemical bonding. The chemical bonding may be formed between the first sensor and the second sensor. Alternatively, the second sensor may be bonded to the first sensor through the film, and the chemical bonding may be respectively provided between the first sensor and the film and between the second sensor and the film. The bonding force between the first sensor and the second sensor may be improved by the chemical bonding. Thus, the sensing device may have the improved stability and durability. The sensing device may be highly integrated and miniaturized.

According to the embodiments of the inventive concept, the first electrode layer may be strongly bonded to the substrate by the first plasma treatment process. Thus, the adhesion layer may be omitted between the substrate and the first electrode layer. The radicals may be formed on the top surface of the substrate by the second plasma treatment process. The exposure process may be performed on the passivation layer so that the passivation layer is chemically bonded to the radicals on the top surface of the substrate. Thus, the bonding force between the passivation layer and the substrate may be improved.

Although the exemplary embodiments of the present invention have been described, it is understood that the present invention should not be limited to these exemplary embodiments but various changes and modifications can be made by one ordinary skilled in the art within the spirit and scope of the present invention as hereinafter claimed embodiments to which various changes are made without departing from the spirit and scope of the present invention are possible. Furthermore, the appended claims should be appreciated as a step including even another embodiment.

What is claimed is:

1. A sensing device comprising:
a first sensor comprising a first substrate, first electrodes, and a first passivation layer; and
a second sensor disposed on the first sensor and comprising a second substrate, second electrodes, and a second passivation layer,
wherein the second sensor is connected to the first sensor through a chemical bonding.

2. The sensing device of claim 1, wherein the first electrodes and the first passivation layer are disposed on a top surface of the first substrate,
the second substrate is disposed on a top surface of the first passivation layer, and
the chemical bonding is provided between the first passivation layer and the second substrate.

3. The sensing device of claim 2, wherein the first passivation layer comprises a fluorine-based polymer, and
the second substrate comprises a fluorine-based polymer.

4. The sensing device of claim 2, wherein the first substrate has a first area and a second area in view of a plane,
wherein the second sensor overlaps the second area of the first substrate in view of the plane, and
the second electrodes are disposed on the first area of the first substrate.

5. The sensing device of claim 1, wherein the first sensor comprises a neural electrode sensor, and the second sensor comprises a chemical sensor or a physical sensor.

6. The sensing device of claim 1, further comprising a third sensor disposed on the second sensor and connected to the second sensor through a chemical bonding,
wherein the third sensor comprises a third substrate, third electrodes, and a third passivation layer.

7. The sensing device of claim 1, wherein the second substrate has a bottom surface that physically contacts a top surface of the first substrate, and
the chemical bonding is provided between the first substrate and the second substrate.

8. The sensing device of claim 7, wherein the first electrodes and the first passivation layer are disposed on a bottom surface of the first substrate.

9. The sensing device of claim 1, wherein the first substrate has first areas and a second area,
the first electrodes are disposed on the first areas of the first substrate,
the first passivation layer covers the second area of the first substrate, and
the first passivation layer is chemically bonded to a top surface of the second area of the first substrate.

10. The sensing device of claim 9, wherein the first substrate comprises a fluorine-based polymer, and
the first passivation layer comprises a photosensitive polymer.

11. A method for fabricating a sensing device, the method comprising:
preparing a first sensor;
performing a first plasma treatment process on a first surface of the first sensor;
performing a second plasma treatment process on a second surface of a second sensor; and
forming a chemical bonding between the first surface of the first sensor and the second surface of the second sensor,
wherein the first sensor comprises a first substrate, first electrodes, and a first passivation layer, and
the second sensor comprises a second substrate, second electrodes, and a second passivation layer.

12. The method of claim 11, wherein first radicals are formed on the first surface of the first sensor by the first plasma treatment process,
second radicals are formed on the second surface of the second sensor by the second plasma treatment process, and
the chemical bonding is formed by reaction of the first radicals and the second radicals.

13. The method of claim 11, wherein the forming of the chemical bonding is performed by a thermocompression process.

14. The method of claim 11, further comprising disposing the second sensor on the first sensor so that the second substrate faces the first passivation layer,
wherein the chemical bonding is formed between the second substrate and the first passivation layer.

15. The method of claim 11, wherein the preparing of the first sensor comprises:
preparing a first substrate having a first area and a second area;
forming a first electrode layer on the first substrate, wherein the first electrode layer directly physically contacts a top surface of the first area of the first substrate;
performing a plasma treatment process on the first substrate and the first electrode layer;

forming a first passivation layer covering the first substrate and the first electrode layer; and performing an exposure process and a development process on the first passivation layer to form a first opening in the first passivation layer, wherein the performing of the exposure process comprises forming a chemical bonding between a top surface of the second area of the first substrate and the first passivation layer.

16. A sensing device comprising:
a first sensor comprising a first substrate, first electrodes, and a first passivation layer;
a second sensor disposed on the first sensor and comprising a second substrate, second electrodes, and a second passivation layer, and
a film disposed between the first sensor and the second sensor,
wherein the first sensor is connected to the film through a first chemical bonding, and
the second sensor is connected to the film through a second chemical bonding.

17. The sensing device of claim 16, wherein the film comprises a photoresist material or perfluoropolyether (PFPE),
the first chemical bonding comprises crosslinked bonding or covalent bonding, and
the second chemical bonding comprises crosslinked bonding or covalent bonding.

18. The sensing device of claim 16, wherein the first substrate has first areas and a second area,
the first electrodes are respectively disposed on the first areas of the first substrate,
the first passivation layer covers the second area of the first substrate, and
the first passivation layer is chemically bonded to a top surface of the second area of the first substrate.

19. The sensing device of claim 16, wherein the first electrodes and the first passivation layer are disposed on a top surface of the first substrate,
the second substrate is disposed on a top surface of the first passivation layer, and
the film is disposed between the first passivation layer and the second substrate.

20. The sensing device of claim 16, wherein the first electrodes and the first passivation layer are disposed on a bottom surface of the first substrate,
the film is disposed between a top surface of the first substrate and a bottom surface of the second substrate, and
the first chemical bonding is provided between the first substrate and the film.

* * * * *